(12) United States Patent
Morrison et al.

(10) Patent No.: US 7,968,117 B1
(45) Date of Patent: *Jun. 28, 2011

(54) EXTERNALLY TRIGGERED MICROCAPSULES

(75) Inventors: Dennis R. Morrison, Kemah, TX (US); Benjamin Mosier, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 456 days.

This patent is subject to a terminal disclaimer.

(21) Appl. No.: 12/100,009

(22) Filed: Apr. 9, 2008

Related U.S. Application Data

(60) Division of application No. 09/079,758, filed on May 15, 1998, now abandoned, which is a continuation-in-part of application No. 08/349,169, filed on Dec. 2, 1994, now Pat. No. 5,827,531.

(51) Int. Cl.
*A61K 8/127* (2006.01)
*A61K 9/48* (2006.01)
*A61K 9/14* (2006.01)
*A61K 9/16* (2006.01)

(52) U.S. Cl. ......... 424/450; 424/451; 424/489; 424/490

(58) Field of Classification Search ................... 424/450
See application file for complete search history.

(56) References Cited

U.S. PATENT DOCUMENTS

| | | |
|---|---|---|
| 2,971,916 A | 2/1961 | Schleicher et al. |
| 4,247,406 A | 1/1981 | Widder et al. |
| 4,345,588 A | 8/1982 | Widder et al. |
| 4,652,257 A | 3/1987 | Chang |

OTHER PUBLICATIONS

Image File Wrapper for U.S. Appl. No. 09/079,758; Entitled: Externally Triggered Microcapsules; filed May 15, 1998; Confirmation No. 8692.
Image File Wrapper for U.S. Appl. No. 11/423,038; Entitled: Externally Triggered Microcapsules; filed Jun. 8, 2006; Confirmation No. 5127.

*Primary Examiner* — Sreeni Padmanabhan
*Assistant Examiner* — Layla Soroush
(74) *Attorney, Agent, or Firm* — Theodore U. Ro

(57) ABSTRACT

Disclosed are microcapsules comprising a polymer shell enclosing one or more immiscible liquid phases in which a drug or drug precursor are contained in a liquid phase. The microparticles also contain magnetic particles that can be heated by application of an external magnetic field and thus heated to a predetermined Curie temperature. Heating of the particles melts the polymer shell and releases the drug without causing heating of surrounding tissues.

19 Claims, 2 Drawing Sheets

EXTERNALLY TRIGGERED MICROCAPSULES

CLAIM OF BENEFIT OF PRIORITY OF PRIOR-FILED CO-PENDING NON-PROVISIONAL APPLICATION

This application is a divisional of commonly-owned U.S. patent application Ser. No. 09/079,758, filed May 15, 1998 now abandoned.

CROSS-REFERENCE TO RELATED APPLICATIONS

This application is a division of U.S. patent application Ser. No. 09/079,758, filed May 15, 1998, now abandoned which is a continuation-in-part of U.S. patent application Ser. No. 08/349,169 filed Dec. 2, 1994 (now U.S. Pat. No. 5,827,531); and this application is related to the following U.S. Patent Applications which are filed contemporaneously herewith:

(1) application Ser. No. 09/079,741 entitled "In situ Activation of Microcapsules" invented by Dennis R. Morrison and Benjamin Mosier;

(2) application Ser. No. 09/079,833 entitled "Microencapsulation and Electrostatic Processing Device" invented by Dennis R. Morrison, Benjamin Mosier and John M. Cassanto;

(3) application Ser. No. 09/079,770 entitled "Low Shear Microencapsulation and Electrostatic Coating Process" invented by Dennis R. Morrison and Benjamin Mosier;

(4) application Ser. No. 09/079,766 entitled "Microencapsulated Bioactive Agents and Method of Making" invented by Dennis R. Morrison and Benjamin Mosier.

STATEMENT REGARDING FEDERALLY SPONSORED RESEARCH OR DEVELOPMENT

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention relates to microcapsules, methods for making microcapsules, encapsulating pharmaceutical compounds in microcapsules, microcapsule encapsulated pharmaceutical compositions and products, and methods of using these compositions. The invention also relates to controlled delivery of a substance contained in a microcapsule through the use of magnetic particles that are heated upon exposure to an electromagnetic field.

2. Description of the Related Art

Although encapsulation of a drug in a microcapsule or other carrier addresses several problems of drug delivery, an area of interest in the art of drug delivery is still the specific, controlled release of the drug from the microcapsule when it reaches the target site. Several approaches have been described to solve this problem, including heating liposomes to the melting temperature of the phospholipid bilayer by inducing local hyperthermia or by heating magnetic powders incorporated into the membranes, and also including physically shaking microcapsules by ultrasound or by oscillating magnetic fields. However, the inventors are aware of no previous method in which a permanent hole is melted in a microcapsule comprising a polymer outer shell, so that the contents are released through the pore.

In a controlled delivery system described by Supersaxo et al. in U.S. Pat. No. 5,470,582, microparticles are made from polymers such as polyesters, polyamides, polyanhydrides and polyacrylates with pre-formed pores and an active agent is allowed to migrate into the microparticles through the pores. After administration, the active agent is released through the pores by diffusion. A burst of release may be caused by application of ultrasonic radiation. Another system, described by Mathiowitz et al. in U.S. Pat. No. 4,898,734, is also based on passive or facilitated diffusion of an active agent from pore-containing polymer microspheres. Methods of facilitating diffusion include exposure to high temperature, light, or ultrasound. This patent also describes degradable microspheres and microspheres immobilized in a polymer matrix. A controlled release delivery system described by Modi in U.S. Pat. No. 5,417,982 is biodegradable copolymer based microspheres in which delayed release of an active agent is controlled by the time required for enzymatic digestion of the polymer matrix. Wheatley et al., in U.S. Pat. No. 4,933,185, describe microcapsules having an inner core and an outer, ionic skin. An active agent and an enzyme are encapsulated in the inner core, such that the enzyme degrades the inner core and releases the active agent.

Controlled release of drugs from liposomes has been achieved by using temperature sensitive polymers in the formation of the liposomes (Magin et al. 1986). Once the liposomes are localized in the target tissue (or tumor) the drug can be rapidly released if the local tissue temperature can be raised above the transition temperature of the liposome membrane. This requires some method of controlled tissue heating which is difficult to achieve without complicated surgical procedures, implanted interstitial antennas or ultrasonics to produce effective local hyperthermia (Hand, 1991). Thermosensitive liposomes have been prepared from a variety of natural and synthetic lipids such as dipalmitoyl phosphatidylcholine, distearoyl phosphatidylcholine, and cholesterol to have transition temperatures of 41-43° C. so that the outer phospholipid membrane melts and releases contained drugs in response to local hyperthermia. Attempts have been made to use these liposomes and local tissue hyperthermia for achieving drug targeting to tumors.

Chelvi and Rathan (1995) prepared temperature-sensitive liposomes from natural lipids, egg phosphatidylcholine:cholesterol (PC:Ch) in a 7:1 molar ratio and ethanol, 6% (v/v) having a transition temperature of 43° C. Fluorescence labeled calcein was encapsulated in the liposomes and administered to mice, a group of whose tumor-bearing legs were immersed in a water bath to achieve a tumor temperature of 43° C. and held there for one hour. Fluorescence microscopy demonstrated the release of calcein from the temperature sensitive liposomes. The in vivo efficacy of temperature-sensitive unilamellar vesicles containing dacarbazine in combination with hyperthermia was detected in murine fibrosarcomas.

Kakinuma et al. (1995) also used thermosensitive liposomes containing cis-diaminedichloroplatin (CDDP) to deliver cytotoxic doses to brain tumors by dissolving the liposomes with localized brain heating. The investigators studied the anti-tumor effect on rat malignant glioma. Ten days after tumor inoculation, the rats were assigned to one of six treatment groups: control, free CDDP, hyperthermia, free CDDP+hyperthermia, liposomes containing CDDP (CDDP-liposomes), and CDDP-liposomes+hyperthermia. Liposomes containing CDDP or free CDDP were injected via the tail vein. Brain tumor heating was administered by means of a radiofrequency antenna designed for rat brain. The rats treated with CDDP-liposome+hyperthermia had the longest survival time and the tumor CDDP level of this group was the highest when compared to the other groups. Histophathological examination showed that tumor cells were necrotized but surrounding normal brain tissue remained undamaged. The greater anti-tumor effects suggested that the combination of thermosensitive liposome and localized hyperthermia better focused anti-tumor drugs to the tumor.

Thermosensitive liposomes designed for drug release by hyperthermia have been tested at different local tissue temperatures (Kakinuma et al., 1996). Four groups were studied: the first received free Cisplatin (cis-diaminedichloroplatin, CDDP); the second received free CDDP and above 41° C. local brain heating for 30 minutes; the third group received liposomes containing CDDP (CDDP-liposomes); and the fourth group received CDDP-liposome and above 41° C. local brain heating for 30 minutes. Brain CDDP levels were significantly higher in group 4, while those in the other groups were undetectable. The present inventors have also studied the distribution of Evans blue dye (Eb) in the artificially heated region of dogs' brain. One group received free Eb and the other group received liposomes containing Eb (Eb-liposome). While the extravasation of free Eb was localized in regions heated to greater than 44° C., that of Eb-liposome was extended up to the regions heated at 41° C. It appears that the use of thermosensitive liposomes and hyperthermia not only contributes to the brain tumor killing as direct thermal killing does, but also helps to increase the concentration of chemotherapeutic drugs into the tumor invaded zones with mild local hyperthermia of only 41° C.

A method of localizing a drug carrier that has been described is the inclusion of magnetic particles in the carrier. The encapsulation of oil-suspended magnetic particles into microcapsules with hydrophilic, organic colloidal membranes is described in U.S. Pat. No. 2,971,916. The magnetic particles were used to direct the microcapsules to a magnetized location on a paper medium, where the capsules were crushed to deliver an ink or stain to the paper.

Microspheres for intravascular administration comprising magnetic particles in a biodegradable carrier are described in U.S. Pat. Nos. 4,247,406 and 4,345,588. The microcapsules described in these patents comprise magnetic particles embedded in a polyamino acid matrix, such as albumin, which also acts as a carrier for a therapeutic drug. The microcapsules are infused into an artery that feeds a particular capillary bed and are then immobilized by the application of a magnetic field across the capillary bed. The microcapsules are held in the bed by the magnetic field until the polymer matrix is dissolved by proteolytic enzymes, or they may be drawn into the surrounding tissues by application of a stronger field. As described in these patents, when these carriers are drawn into tissue in order to directly deliver the drugs, they become immobilized in the tissue where they remain after the field is terminated.

Liposomes encapsulating magnetic particles are described by Chang in U.S. Pat. No. 4,652,257. These liposomes are also used to localize a chemotherapeutic drug in a capillary bed by application of a magnetic field. After the liposomes are immobilized at the target site, the magnetic particles are vibrated by application of an oscillating magnetic field. The particles are vibrated in order to destabilize, or to rupture the lipid membrane, thus releasing the drug. The liposomes described by Chang are small (on the order of 1-2 micrometers with ferromagnetic particles of about 100 to 1000 angstroms), and are further limited in that only hydrophilic drugs can be delivered from the liposomes. The small size of these liposomes limits their utility because the size and shape is a factor in the distribution and drug delivery of the liposomes in the tissues. Additionally, in the liposomes described by Chang, it is the mechanical force of the vibrating ferromagnetic particles that destabilizes or ruptures the membrane, rather than any local heating effect.

It is evident, therefore, that improvements are still needed to address certain drawbacks of conventional liposome or microcapsule delivery systems. Delivery of a variety of active drugs to a specific site in the body with a liposome formulation still presents difficulties, for example. There is a need for a system that would address certain disadvantages of thermosensitive liposomes for drug delivery. These delivery systems are primarily useful for drugs that diffuse out of the carrier across the outer phospholipid bi-layer membrane, or in liposomes that are phagocytized by a particular cell type. Thermosensitive liposomes may be melted by local hyperthermia, but unfortunately, methods for creating hyperthermia in local tissues are not precise and are largely dependent on the local tissue composition. Heating may also be counteracted by blood flow cooling. Thermosensitive liposomes (or microcapsules) are limited to those having outer membranes that can be melted at temperatures below those that cause permanent damage to healthy tissues, usually a maximum of 41-44° C. In those methods in which heating or mechanical forces are used to disrupt or melt the liposome membrane, or even melt a hole in the membrane, the phospholipid bilayer will rapidly extend to close off the hole and thereby re-form the lipid bilayer. There is a need, therefore for a method of controlled delivery of a drug at the tumor site without depending on passive diffusion, local hyperthermia of tissues, or temporary phase changes in the outer membrane.

BRIEF SUMMARY OF THE INVENTION

The present invention addresses these and other drawbacks in the prior art by providing compositions and methods comprising multi-layered liquid microcapsules that are composed of a polymeric outer skin or membrane surrounding immiscible fluid compartments containing drugs in either solid, crystalline or dissolved states. The microcapsules may also contain metal particles such as ferromagnetic particles or other magnetic particles that become heated by induction to a controllable temperature when exposed to an external electromagnetic field or other forms of activating energy. The microcapsules are designed so that the magnetic particles may be heated to their characteristic Curie temperature (Curie point) by exposure to an electromagnetic field, and will melt holes in the outer skin of the microparticles, designed to have a melting temperature that is less than the Curie temperature, thus releasing the contents (drugs) without causing widespread damage to the surrounding tissues. These magnetic particles typically have a size range of 0.01 to 50 microns, and preferably not more than 1/10 of the diameter of the microcapsule containing the magnetic particle.

The magnetic particles that are contained in the microcapsules have a specific absorption rate (SAR) when exposed to an electromagnetic field, which is different from that of normal cells or tissues, and the particles may be designed to have a characteristic maximum temperature (Curie point), at which the magnetic material loses it thermal conductivity or magnetic permeability and will not heat further upon continued exposure to the magnetic field. The microcapsules are also designed so that the melting temperature of the outer polymeric skin or membrane of the microcapsules is less than the Curie point of the magnetic particles within that microcapsule.

The magnetic particles may be composed of a variety of metals including ferromagnetic particles, such as $Fe_3O_4$, iron carbonyls and combinations of various transition metal oxides. The inventors have demonstrated the utility of ceramic coated particles comprising oxides of iron, nickel and zinc, such as particles comprising about 66 wt % $Fe_2O_3$, about 9 wt % NiO, and about 25 wt % ZnO. Additional metals that may be used in the particles described herein include, but are not limited to cobalt, copper, gold, silver and combinations thereof, including copper containing gold and silver alloys. The magnetic material used in microcapsules as described herein is also typically covered by a material such as a ceramic that is compatible with the liquids within the microcapsule and with the drug or active agent. Although the particles described herein are coated with ceramics, other coatings that are compatible with the liquid phases and drugs or solvents to be used in the microcapsules. Ceramics were chosen for the exemplary microcapsules described below because of their low antigenicity, they are not chemically reactive with the solvents or drugs used in the microcapsules, and the protect the metal from oxidation. Alternate coatings would include, but not be limited to methacrylates, alginates, dextran, polyacrylates, polyvinyl pyrrolidone (if the ferrous material is fully oxidized).

For use in clinical applications, the particles may have a Curie temperature of from about 41°-44° or even up to as high as about 80 to 95° C. Such high temperatures may be utilized in the microcapsules because the small magnetic particles are a point heat source rather than a tissue hyperthermia technique, which could never be used at such high temperatures without causing extensive tissue damage. With the microcapsules of the present invention, it is contemplated by the inventors that even a Curie point of 95° C. would cause collateral damage in only a few neighboring cells. In the practice of the invention, one may use an electromagnetic field with a frequency of about 85-95, or even about 100 kHz, a strength of about 1500-2000 Amps/m, although frequencies below about 500 KHz are also acceptable.

Certain compositions may also contain mixtures of microcapsules in which some capsules contain particles with different Curie temperatures than others, or microcapsules with polymer membranes that have different melting temperatures so that one can effect multiple releases of drug with a single infusion. Of course, one may release different drugs at different temperatures, or one may effect multiple releases of the same drug. This allows a physician to release part of the drug under control of an electromagnetic field, and then later release more drug by using a different field power or time, or to release different drugs separately, still from a single infusion or injection. The invention, therefore, provides a flexibility that is a distinct advantage over prior methods of controlled delivery.

In a method of using the microcapsules, after the microcapsules reach a target site such as a tumor, either by direct injection or infusion, the microcapsules are exposed to an external electromagnetic field that is tuned to the maximum SAR of the magnetic particles contained in the microcapsules. This method may include exposure of microcapsules entrapped in tissues of a subject where the exposure is by external administration of the electromagnetic field through the subject's skin and outer tissues. This energy is absorbed by the magnetic particles which are heated to their Curie temperature without heating the surrounding tissue. The heated magnetic particles melt a hole or perforation in the outer skin of the microcapsules, thereby lysing the microcapsules and providing a conduit for rapid release of the drug by bulk fluid flow out of the microcapsules and/or diffusion of the drug out of the hole created in the membrane. The released drug is then in contact with cells at the local site. It is understood that, although the heating of the particles within the microcapsules does not require heating of the local tissue, that the compositions and methods described herein may be used in conjunction with local hyperthermia therapies where desired. In certain embodiments, the microcapsules may be exposed to an electromagnetic field of up to 500 KHz, and in certain embodiments, around 100 KHz, or alternatively to from about 6.78 to 27.12 MHz radiofrequency, from about 915 to about 2450 MHz microwave radiation, or to ultrasound.

In the practice of the invention, virtually any drug may be encapsulated, including both hydrophilic and lipophilic drugs. Certain embodiments include the encapsulation of an anti-cancer drug, such as cis-platin, doxorubicin, daunorubicin, paclitaxel, aziridinylbenzoquinone, muramyltripeptide, 5-fluoruracil, and other types of drugs that would include, but not be limited to anesthetics, systemic antibiotics, antiparasitics, systemic quinolones, anti-infectives, anti-inflammatories, aminoglycosides, cephalosporins, penicillins, antidotes, anti-cholinesterases, metal poisoning antidotes, antineoplastics, cytotoxic agents, hormones, steroids, immunomodulators, cytokines, interleukins, systemic antivirals, systemic antifungals, biologicals, alpha-antitrypsin, bone metabolism regulators, hypercalcemic agents, cardiovascular agents, beta blockers, cerebral vasodilators, cerebral metabolic enhancers, cholinesterase inhibitors, colony stimulating factors, granulocyte-colony stimulating factors, granulocyte macrophage-colony stimulating factors, vasopressors, local diabetic agents, diagnostics such as CT scan enhancers and angiocardiography agents, adenosine deaminase deficiency agents, gonadotropin inhibitors, adrenal cortical steroid inhibitors, gonadotropin releasing hormone stimulants, vasopressins, urofollitropins, muscle relaxants such as neuromuscular blocking agents, prostaglandin analogs, prostaglandins, prostaglandin inhibitors, respiratory therapy agents, anticholinergics, beta andrenergic stimulators, sympathomimetics, and thrombolytics. In certain embodiments, the drugs may be enzymes, or proenzymes that may be encapsulated and activated by mixing as described in a related application by the same inventors, entitled "In Situ Activation of Microcapsules" incorporated herein by reference. In addition to the methods of mixing immiscible layers described elsewhere, in microcapsules containing magnetic particles, one can facilitate internal mixing by exposing the microcapsules to an oscillating magnetic field.

As such, certain embodiments of the present invention may be described as methods of treating a tumor in a subject comprising: obtaining a pharmaceutical composition comprising a plurality of microcapsules in a pharmaceutically acceptable solution, each microcapsule comprising two or more immiscible liquid phases enclosed in a polymer shell having a melting temperature, magnetic particles within the microcapsules having a Curie temperature higher than the melting temperature of the polymer shell, and contained in a liquid phase in contact with the polymer shell, and an anti-cancer drug contained in a liquid phase; administering the pharmaceutical composition to the subject in a manner effective to place the microcapsules within or adjacent to the tumor; and applying a magnetic field to the microcapsules effective to heat the magnetic particles to their Curie temperature and melt at least a portion of the polymer shell.

In certain embodiments of the invention, the microcapsules may also contain a radiocontrast media, or a medium that becomes radio-opaque through a change of oxidation state when exposed to energy. The radiocontrast media to be used may include, but is not limited to a halogenated oil, such as for example, halogenated poppy seed oil, cotton seed oil, soybean oil, safflower oil, corn oil, olive oil, sunflower seed oil, sesame seed oil, or canola oil.

The microcapsules of the invention can be separated by filtration or other means known in the art to obtain a population of microcapsules of a particular size range that is preferred for a particular use. Typically, microcapsules of 1-20 micron diameter are optimum for intravenous administration, whereas, 50-300 micron diameter microcapsules are used for intraarterial delivery and 300 micron or greater for intraperitoneal administration. In each size range, highly uniform microspheres are needed for maximum packing densities and maximum drug payload delivery to target organs or tumors. Therefore, one may obtain microcapsules of from about 1 to about 500 microns in diameter, or from about 300 to about 500 microns in diameter, or from about 30 to about 50 microns in diameter, or even from about 1 to about 20 microns in diameter. As is known in the art of chemo-embolization, particles of a certain size will form a part of an embolization in different areas such as the arterial, lung capillaries, venous, or even peritoneal systems of a body. Microcapsules may be designed, then to be used in a chemo-embolization application, or they may be designed to pass freely through the capillaries or circulation of a subject in order to reach a target site. In the practice of the invention, one may choose microcapsules of a particular size so that the microcapsules will occlude an arterial or venous vessel, for example at the site of a disease. Such a disease site may be a thrombosis, a wound, a site of infection, a lipid deposit or even the vasculature of a tumor. Because the microcapsules contain magnetic particles, they may also be localized by application of an electromagnetic field as is known in the art, except that care must be taken not to heat the particles prematurely.

The drug precursors of the present invention are in certain cases a proenzyme or a zymogen. A proenzyme is an inactive enzyme precursor that can be activated by cleavage of one or a few specific peptide bonds. In certain embodiments the proenzyme may be a pro-thrombolytic enzyme, or a pro-urokinase, or a pro-tissue plasminogen activator.

Certain embodiments of the invention will include the use of fluorinated pyrimidine or purine analogs such as the prodrug Floxuridine (Fluorodeoxyuridine) which is converted to the inhibitor 5'-monophosphate nucleotide (F-UMP) by thymidine kinase. Other embodiments may utilize the oxidation, reduction or hydrolysis of a prodrug that results in activation, change in activity or in conformation. Another example may be the use of the prodrug 6-mercaptopurine, which is activated to 6-mercaptopurine ribonucleotide, the oxidation of trimethadone to the active agent, dimethadione, the oxidation of phenacetin to methemoglobin, or the reduction of chloral hydrate to trichloroethanol. In addition, active agents may be produced in microcapsules by contact with lipid soluble enzymes such as those isolated from the hepatic microsomes, or they may use doxorubicin derivatives activated by lysozyme.

As described herein certain inventions of the present disclosure may be compositions comprising a microcapsule comprising two or more immiscible liquid phases enclosed in a polymer shell, a drug precursor and possibly a drug activator, wherein the drug precursor and drug activator, when present, are contained in separate immiscible liquid phases, a magnetic particle with a Curie point higher than the melting temperature of the polymer shell and further wherein the microcapsule is made by the method comprising: formulating a first phase comprising a first solvent, a first polymer soluble in the first phase and insoluble in a second phase, a co-solvent, oil, and water; formulating the second phase immiscible with the first phase, the second phase comprising a second solvent, a second polymer soluble in the second phase and insoluble in the first phase, a surface active agent, and a salt; the surface active agent having a hydrophilic/lipophilic balance value greater than that of the first polymer; the second polymer having a hydrophilic/lipophilic balance value lower than that of the surface active agent; creating an interface between the first and second phases in a manner that limits fluid shear to between about 1 to 100 dynes/cm$^2$, if carried out under conditions of greater than or about equal to 1 gravity, or between about 2 to 30 dynes/cm$^2$, if carried out under conditions of less than or about equal to $1 \times 10^{-2}$ gravity, and maintains adsorptive surface characteristics at the interface. It is understood that the magnetic particles are contained in the liquid layer that lies next to the membrane, which may be an aqueous or hydrocarbon layer depending on the particular application.

Processes and compositions are provided by the present invention which overcome certain of the limitations of prior methodology for forming microcapsules. In particular, methods and compositions are provided which form multilamellar microcapsules having alternating hydrophilic and hydrophobic liquid layers, surrounded by flexible, semi-permeable hydrophobic, outer membranes which can be tailored specifically to control the diffusion rate. In particular, the methods of making microcapsules provided by the present invention do not rely on batch processes such as density-driven phase separation and stratification into horizontal layers, mechanical mixing or solvent evaporation. Encapsulation of cytotoxic or labile drugs in such microcapsules enables targeted delivery and sustained release kinetics that are not currently available with intravenous injection.

The invention provides, in one aspect, methods of making a multi-layered microcapsule. The term microcapsule as used herein is a general term which can include any spherical microscopic vesicle including microspheres, micelles, inverted micelles, bilayer vesicles and liposomes. The term microcapsule as used herein is also a more specific term which refers to a microcapsule that comprises at least two layers, one of which is innermost and is substantially completely enclosed within the other. In a distinct break from traditional methods for making microcapsules, the methods of the invention rely on low fluid shear, interfacial coacervation and liquid-liquid diffusion process, particularly as developed for forming microcapsules that may contain both aqueous and hydrocarbon soluble drugs.

The terms multi-layered and multi-lamellar are used interchangeably throughout the specification and claims and both refer to the fact that the microcapsules of the invention comprise at least two immiscible layers nested around one another. In some instances, the core layer will be hydrophobic in nature and will be completely surrounded by at least one neighboring hydrophilic layer. In others, the core layer will be hydrophilic in nature and will be completely surrounded by at least one neighboring hydrophobic layer.

The basic method of the invention relies on liquid-liquid interactions. In the basic method, the first step entails formulating a first phase or layer while the second step entails formulating a second phase or layer. The two phases or layers are formulated to be immiscible with one another. For the purposes of this invention, "immiscible" means that due to differences in density, viscosity or surface tension, the two adjoining phases or layers form an interface resembling a meniscus, and furthermore that the solubility of any component in one phase is not more than 10 gm/100 ml in the second, adjoining phase or layer.

Formulating the first phase or layer comprises combining a first solvent, a first polymer soluble in the first phase, a co-solvent, an oil, and water. The first solvent will typically comprise about 75-90% by volume of the first phase. The first polymer is selected to be one soluble in the first phase and typically will comprise about 1-5% by volume of the first phase. A small amount of a co-solvent is also added to the first phase, which co-solvent may also function as a co-surfactant. Oil comprising about 1-10% by volume is also added to the formulation. The first phase will also contain about 1-5% water by volume.

The method next calls for formulating a second phase immiscible with the first phase. The second phase comprises a second solvent, a second polymer soluble in the second phase, a surface active agent, and a salt. The relative, approximate volume percentages of these constituents is about 70-98% second solvent, 1-10% second polymer, 1-4% surface active agent, and 0-3% salt.

In order to ensure that the liquid-liquid interactions necessary to form the microcapsule will occur, certain of the constituents of each phase are selected relative to one another. Thus, the surface active agent in the second phase is selected such that it will have a hydrophilic/lipophilic balance value greater than that of the first polymer constituent of the first phase. Generally, the most useful surface active agents have been found to be those which are nonionic and which have a hydrophilic/lipophilic balance value of 10.0 or greater. Next, the second polymer constituent of the second phase is selected to have a hydrophilic/lipophilic balance value lower than that of the surface active agent constituent of the same phase. While not an exhaustive list, certain hydrophilic/lipophilic balance values of materials which may be used in the formulations of the invention are provided below.

Hydrophilic/Lipophilic Balance (HLB)
(McCutcheon 1979)

| Compound | HLB |
| --- | --- |
| Glycerol trioleate | 0.8 |
| Cholesterol | 1.0 |
| Triglyceride of coconut oil | 1.4 |
| Sorbitan trioleate | 1.8 |
| Sorbitan tristearate | 2.1 |
| Glycerol monooleate | 2.7 |
| Mono and di glycerides of fat burning fatty acids | 2.8 |
| Glycerol Monostearate (gms) | 2.8-5.0 (3.8 preferred) |
| Propoxylated ethylene diamine plus ethylene oxide | 3-28 |
| Mono/diglyceride | 3.2 |
| Glycerol mono coconut | 3.4 |
| Mono/diglyceride | 3.5 |
| Propylene glycol mono fatty acid ester | 3.5 |
| Monoethoxyl lauryl ether | 3.6 |
| Stearyl lactyl acid | 3.8 |
| Hydrogenated cottonseed oil | 3.8 |
| Sodium lauryl sulfate | 4.0 |
| Mono and diglycerides with citric acid or lactylic ester or fatty acid | 4.2-4.6 |
| Ethoxylated fatty amine (2 moles ETO) | 4.5 |
| Diethylene glycol monostearate | 4.7 |
| Sorbitan monopalmitate | 4.7 |
| Diethylene glycol monostearate and oleate | 4.7 |
| Ethoxylated (2) cetyl ether | 5.3 |
| Glycerol Monoricinoleate | 6.4 |
| Glycerol monolaurate | 6.8 |
| Triglycerol mono stearate | 7.0 |
| Polyethylene glycol (400 dioleate) | 7.2 |
| Lanolin sterol | 8.0 |
| Ethoxylated nonyl phenol (CO-420 & CO 850) | 8.0-16.0 |
| Polyethylene glycol (400) distearate | 8.2 |
| Sorbitan monolaurate | 8.6 |
| Ethoxylated sorbitan fatty acid esters and alkyl/aryl alcohol | 9.0 |
| Anhydrous lanolin | 10.0 |
| Polyethylene glycol monostearate | 11.0 |
| Polyethylene glycol 400 | 11.2 |
| Ethoxylated (10) cetyl ether | 12.9 |
| Ethoxylated glycerol monostearate (gms) | 13.1 |
| Sorbitan monostearate | 14.9 |
| Sorbitan monooleate with 20 moles ethylene oxide | 15.0 |
| Ethoxylated (20) oleyl ether | 15.3 |
| Ethoxylated (20) stearyl cetyl ether | 15.8 |
| Ethoxylated castor oil | 18.0 |
| Nonyl phenol polyethylene glycol ether | 18.1 |
| Polyethylene glycol 600 mono laurate | 19.6 |
| Sodium lauryl sulfate | 40 |
| Propylene glycol monostearate | 40 |
| Hydroxylated lanolin sodium oleyl sulfate | 42 |
| Blends of GMS and sorbitan monooleate with 20 mols ethylene oxide | 52 |

The basic method next involves creating an interface between the first and second phases. The creation of the interface is achieved in such a way that minimal shear and mixing occurs between the phases. The two immiscible phases are brought together in such a mechanical manner that the fluid shear properties are controlled to low levels, typically below about 12 dynes/cm$^2$, and such that the adsorptive surface properties at the immiscible interfaces are not significantly altered. Although the exact mechanisms are not fully understood, the inventors believe that the maintenance of certain surface properties, such as the surface tension, Helmholtz charge distribution (electrical double layer), and partitioning of the surfactant molecules between the immiscible phases must remain substantially intact so that lateral phase separation can occur in a manner which allows simultaneous formation of multiple liquid interfaces (oil/water or water/oil) and which results in microcapsules having alternating spherical shells of hydrophilic and hydrophobic liquid layers. This is believed to be the mechanism for the formation of multilamellar vesicles which are formed in a single step. Although this can best be demonstrated under microgravity conditions, wherein buoyant convection is absent and diffusion-driven convection and surface tension differences predominate, this also can be accomplished in unit gravity conditions by balancing the density differences between the two liquid phases or by any other mechanical means which prevents excess fluid shear from significantly altering the normal adsorptive surface properties which are determined by the chemical composition of the formulas and the interfacial phenomena among the solvents, polymers and surfactants. In a preferred embodiment, the creation of the interface will occur by sliding individually separated compartments containing the two phases into register with one another in a manner that substantially limits shear and provides gentle mixing.

In the final step of the basic method, conditions are established in order to substantially limit all mixing between the interfaced liquid phases. In the most preferred environment, the two phases would be allowed to interact at their interface without agitation, stirring, shearing or like force. It is preferred to also limit even those quiescent forces such a gravity-controlled sedimenting, phase separation into stratified layers, shifting, drift and the like. Thus, in certain preferred embodiments, only chiefly diffusion-driven convection and interfacial coacervation is used to spontaneously form microcapsules, as the chemical formulations of the different phases assist in lowering the surface free energy across the interface. It is also at this time that formation of the polymeric outer coating is initiated.

In one embodiment, the two liquids thus formulated are separated into distinct compartments or spaces which spaces are each connected to a central diffusion chamber into which each compartment can deliver its resident liquid loading. The compartments are initially closed to access into the central diffusion chamber so that the first and second liquids are kept apart from one another and not allowed to interact. While it is possible to use any number of devices to achieve this separation, a preferred device is a device like the Materials Dispersion Apparatus (MEPS) described in more detail elsewhere. Preferred devices are also described in a related US Patent Application by the same inventors and John M. Cassanto filed concurrently with the present application and entitled, "Microencapsulation and Electrostatic Processing Device." The separation of the two liquids is maintained until both liquids and the device containing them can be placed in an environment in which convective mixing may be minimized, such as in a microgravity environment.

The methods of the invention are slightly different depending upon whether the first solvent is selected to be organic or aqueous. Where an organic solvent is used to formulate the first phase, that organic solvent is selected from the group of organic solvents consisting of ethyl alcohol, methyl alcohol and isopropyl alcohol. Where an organic first solvent is used to formulate the first phase, the first polymer is selected to be one soluble in the organic solvent selected. Such a first polymer may be selected from the group of polymers consisting of glycerol monosterate, glycerol monooleate, glycerol monolaurate, glycerol dioleate, glycerol disterate, cholesterol, stigmasterol, phytosterol, campesterol, and lecithins such as phosphatidyl cholines (e.g., Centrolex-F®).

Where the first solvent is aqueous, a slightly different approach is taken. In those instances, the first polymer is again requisitely soluble in the first aqueous phase and may be selected from the group of polymers consisting of polyvinyl pyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins.

Regardless of the formulation with an aqueous or organic first solvent and polymer, the methods of the invention both use a co-solvent which may be selected from the group of co-solvents consisting of $C_3$-$C_8$ alcohols, tetrahydrofuran, dioxane, acetonitrile, dimethylformamide, dimethylacetamide, and dimethyl sulfoxide. Similarly regardless of the organic/aqueous nature of the first solvent and polymer used, the methods of the invention add to the formulation of the first phase an oil. These oils may be selected from the group of oils consisting of unsaturated oils such as poppy seed oil, olive oil, peanut oil, sesame oil, cotton seed oil, soybean oil, safflower oil, corn oil, sunflower seed oil and canola oil or saturated oils such as mineral oil, long chain paraffinic oil, and liquid petrolatum. In a preferred embodiment, poppy seed oil will be halogenated, or in certain embodiments, iodinated to form iodinated poppy seed oil (IPO) and incorporated into a microcapsule as a marker or tracer for tracking the presence of the microcapsule once injected via radiocontrast detection methods known well to those of skill in the art of radiography.

Whether the method involves an organic or an aqueous first solvent, the second polymer, the surface active agent and the salt may each be selected from a particular group of such compounds. The second polymer may be selected from the group of polymers consisting of polyethyleneglycol 400-20000 daltons, dextran 1000-100,000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, carboxypropyl cellulose, and lecithins. The surface active agent is selected from the group of surface active agents consisting of sorbitan monooleate treated with ethylene oxide, dextran, polyethylene glycol, $C_{12}$-$C_{20}$ fatty acids, 2-amino-2-methyl-1-propyl aminomethyl propanol amphoteric salts and quaternary ammonium salts. The salt is selected from the group of salts consisting of NaCl, KCl, $CaCl_2$, $MgCl_2$, quaternary ammonium salts such as cetyl trimethylammonium bromide and 4-methoxy-4(3-phosphatidyl choline)spiro(1,2-dioxetane-3-g,1-adamantane) disodium salt.

Multi-layered microcapsules, with both hydrophobic and hydrophilic drug compartments, as produced by the methods of the invention enable diffusion of complimentary drugs from the same microcapsule, e.g. antibiotics and immunostimulants to treat resistant infections or multiple fibrinolytic drugs to dissolve emboli. Co-encapsulation of radio-contrast medium as provided herein enables oncologists to monitor the delivery of anti-tumor microcapsules to target tumors using computerized tomography and radiography that track the distribution of microcapsules after release from the intraarterial catheter. Such microcapsules will have important applications in chemotherapy of certain liver, kidney, brain and other tumors.

The diameters of microcapsules possible to attain using the methods of the invention are also of particular usefulness in medical applications. Thus, whereas prior art methods have been able to routinely produce microcapsules over 1-10 micron average sizes, the present invention's methods provide similarly-sized microcapsules of 1-20 micron diameters for intravenous administration. Also provided are 25-300 micron sized microcapsules particularly useful in interarterial chemoembolization of tumors, and microcapsules in the range of 300 micron and greater diameters useful in interperitoneal or intramuscular administered drugs.

The pharmaceutical composition encapsulated in the microcapsule may be one soluble in aqueous solutions or may be one soluble in organic solutions. This, of course, governs the selection of the phase or layer in which the pharmaceutical composition is formulated. The microcapsules of the invention and methods for producing them are of particular utility when formulating organic-soluble drugs as these types of drugs are otherwise very difficult to administer. The pharmaceuticals may be those selected from the group of such widely diversified pharmaceutical compositions as that consisting of cytotoxins, proteases, cytokines, anti-nauseants, steroids, anti-fungal agents, fibrinolytic enzymes, and antibiotics. The inventors have successfully encapsulated representatives of these classes of pharmaceuticals using the methods of the invention. It is also possible to incorporate a pharmaceutical composition which is not initially dissolved in one or another of the phases or layers, but rather which drug is in suspension. As noted above, depending upon its solubility and upon where the pharmaceutical chemist wishes to locate the drug, it is possible to formulate a drug in any of the phases or layers, by dissolving or suspending the drug as needed. Upon melting of the polymer shell by heating the magnetic particles, any of such layers and their contents will leak out of the microcapsule.

The methods of the invention surprisingly demonstrated the ability to package very high concentrations of drugs in the layers formed. It is possible, using the methods of the invention, to formulate a pharmaceutical at a concentration sufficient to allow nascent crystal formation within the microcapsule once it is formed. These microcapsules, due in one regard to their being constructed with outer polymeric coatings, are also particularly flexible yet rugged (able to withstand shear forces greater than 10 dynes/cm$^2$). As will be related specifically below, microgravity experiments, on sounding rockets (1989-92) and Shuttle missions STS-52 (1992) and STS-56 (1993) using an automated Materials Dispersion Apparatus, produced multi-lamellar microcapsules containing both Cis-platinum (anti-tumor drug) and iodinated poppy seed oil (a non-radioactive, radiocontrast medium), surrounded by a polymeric skin. Microcapsules formed with amoxicillin (antibiotic) or urokinase (a clot dissolving enzyme), co-encapsulated with IPO, were still intact after two years after return to 1×g environments. In many instances, microcapsules were formed with the Cis-Platinum or amoxicillin so concentrated that crystals of the drugs formed inside.

In certain embodiments of the methods of the invention, pharmaceutical compositions will be incorporated into the microcapsule. Where such pharmaceuticals are thusly incorporated, they may be introduced initially as a solute or as particulates suspended in one or the other of the liquids used to formulate the layers of the microcapsules. In certain embodiments, the pharmaceutical is introduced in one of the phases or layers used to produce the microcapsule at a concentration sufficient to allow nascent crystal formation within said microcapsule. Crystal formation may occur at or near the time of formation of the microcapsule containing the dissolved pharmaceutical material. The aqueous solvent system used to dissolve an aqueous-soluble pharmaceutical is selected to permit water molecules to migrate away from the drug-containing layer into the alcoholic mixture. The process of crystal formation is likely to be promoted in this manner after formation of the microcapsule. In fact, it is possible to enhance the crystallization process after the microcapsule is formed by controlled transport of the solvent phase or layer in which the pharmaceutical to be crystallized is a solute. In certain embodiments, the crystal thus formed may take up most of the internal capacity of the microcapsule.

Surprisingly, the methods of the invention have demonstrated a unique ability to encapsulate such saturated drug solutions, and since the overall partitioning characteristics between immiscible layers facilitates solvent transport out of the aqueous layer, it is possible to concentrate the drug to the point that formation of drug crystals occurs within the microcapsules. This ability of the microcapsules and methods of the invention provides the maximum drug payload per microcapsule and the best drug release kinetics for prolonged treatment at maximum drug diffusion rates.

Microcapsules containing a large volume component of crystalline drug provide the most concentrated drug possible when it is released at the target site. Until the crystals are completely dissolved, the drug release rate is independent of time (zero order release kinetics). When the crystals have dissolved, the drug release rates revert to first order kinetics (exponential with time). The encapsulated crystals of the invention are in the range of 1-100 microns along one face. Since these crystals are precipitated in situ, they are quite different from the other commercially-available crystalline drug delivery systems (e.g., Microcrystal®) which use phospholipids to encapsulate tiny particles or crystals of drugs with an average diameter of only 0.3-1.0 micron [Parikl and Stern 1994].

It is also possible to additionally treat the microcapsules thus formed with additional steps. In some instances, the methods of the invention, regardless of whether they initially use an organic or an aqueous first solvent, formulate a third phase comprising an oil or $C_{20}$-$C_{38}$ paraffin and, contact the formed microcapsule with the third phase. In other instances, the methods of the invention form a two-layered microcapsule, then formulate a third phase comprising an aqueous solution and, contact the formed microcapsule with the third phase. The basic method and alternatives are summarized below.

| | Group 1 | Group 2 |
|---|---|---|
| Solution 1 | Solvent 1 is a hydrocarbon Polymers are hydrocarbon soluble, selected to form the outer coating (typically of lower HLB values) | Solvent 1 is aqueous Polymers (skin) are water soluble, but can be extended into organic phase (includes phospholipids) Ex. Centrolex F ® |
| | Co-solvents alcohols, hydrocarbons (act as co-surfactants) | Co-solvents same, but often less % |
| | Oils saturated or unsaturated oils Prodrug or activator dissolved (or suspended particulate) | Oils same Prodrug or activator dissolved (or particulate) |
| Solution 2 | Solvent 2 aqueous | Solvent 2 same |
| | Polymers water soluble (PEG, Dextran) | Polymers same |
| | Surfactants (typically higher HLB value) | Surfactants same but often less % |
| | Salts ionic, quaternary ammonium salts | Salts same, but often different % |
| | Prodrug or activator aqueous soluble | Prodrug or activator aqueous soluble |
| Solution 3 | Oils hydrocarbons | Oils same |
| | Polymers hydrocarbon-soluble | Polymers same |
| | Drugs can be included | Drugs can be included |
| | --OR-- | --OR-- |
| | Alternative aqueous solution coating—adjuvants immunoglobulins polymers—aqueous soluble surfactants— | Alternative aqueous solution coating same polymer same surfactants same |

Traditional emulsion methods form a O/W/O (oil/water/oil) or W/O/W (water/oil/water) liquid system which is designed to retain the internal phase(s) within the external solvent unless the emulsion is broken, whereupon the liquid phases separate. In the methods of the invention, the use of surfactants and co-surfactants permits formation of an emulsion of large spheroids (not small microspheroids) of one phase dispersed in the other phase configured in a sphere. The sphere is also surrounded by another immiscible liquid layer (opposite phase to that of the innermost liquid sphere) and then (often) this multi-layered sphere is contained in another opposite-phase liquid layer and finally the entire multi-layered sphere is contained in an outer skin. The results of the process of the invention are not to form a traditional O/W/O or W/O/W emulsion (which is a fine dispersion of one phase in another), but rather to form multi-lamellar, alternating immiscible-layer microcapsules contained within a thin, semi-permeable outer skin. In the microcapsules of the invention, the immiscible phases are distinct and separated according to the surface tension characteristics of the liquids at each interface, hence there is no true emulsion maintained by the surfactant which could be broken.

Thus, in certain embodiments of the methods and compositions of the invention, the multi-layered microcapsule will be produced which comprises at least three alternating layers or phases. Thus, if the first layer is an aqueous layer or core, the next layer may be an organic layer. This organic layer may then be covered over by a second aqueous layer which forms on its outer surface a polymeric skin. Conversely, the liquid at the core of the microcapsule may be an organic liquid layered over by an aqueous layer followed by another organic layer which forms a polymeric skin over the surface of the microcapsule. Certainly, extension of these basic formulations may be envisioned where four or more layers are possible or where multiple skins or coatings are utilized.

Whether used in conjunction with a two-layer microcapsule or with microcapsules with more than two layers, the coatings of the present invention are of substantial utility, particularly when the methods are carried out at Earth-normal gravity. The coatings can be either substantially of a hydrophobic nature or of a hydrophilic nature as described below and are derived from addition of certain polymers in the initial formulations of the liquids used to make the microcapsules. Where hydrophobic coatings are used in conjunction with drug-delivery systems, the coatings are selected for their complementary permeability to the drug to be delivered. The polymers are also selected for their flexible characteristics after formation and curing which is of particular utility during intravascular transport and allows higher packing densities for forming emboli such as in chemoembolization therapy. Thus, for example where a water-soluble drug is to be delivered, the drug is contained in an inner aqueous layer over which is placed a coating permeable to the dissolved drug. In alternate embodiments, the drug may be more hydrophobic and will be contained in a hydrocarbon layer within the microcapsule. In either embodiment the drug may actually be a prodrug, and an activator may be contained in a layer immiscible with the layer containing the prodrug. Preferably, the coating material should be impermeable to solvents or oils. The coatings which have been observed to be deposited on the surfaces of the microcapsules of the invention are about 0.01-2.0 microns thick where the coating is a hydrophobic coating, and about 0.1-5.0 microns thick where hydrophilic coatings are deposited.

The additional steps and third formulated phases may also be used advantageously to provide the microcapsule with specific characteristics. Thus, the third phase may further comprise a pharmaceutical composition which is added to the formed surface of the microcapsule. The third phase may also be used to add a pharmaceutical composition such as an adjuvant. The adjuvant may further comprise an immunoglobulin, other protein, hydrocolloid or polysaccharide. This is of particular utility in designing microcapsules with unique immunologic, proteinaceous, surface charged, or other surface characteristics which makes them selectively adhere to certain target tissues (cells) or renders the microcapsules attractive to certain phagocytic cells (when the cells are the actual target for the therapeutic drug). Where the adjuvant is a hydrocolloid, it may be selected from the group of such hydrocolloids consisting of collagen, isoelectric gelatin, agar, gum arabic, gum tragacanth, alginates, cellulose derivatives, guar gum, cyclodextrins, and carrageenans. The third phase may also further comprise a surface active agent.

The third aqueous phase can also contain a chemical activator which acts upon the inactive form of the pharmaceutical agent (drug) as it diffuses out of the inner layers of the microcapsule. The function of the activator is to chemically convert the inactive drug to its active form just before it is released from the microcapsule. This is illustrated when the pharmaceutical is a pro-enzyme and where the activator is another proteolytic enzyme which cleaves the pro-enzyme at active site to render the molecule biologically active. This embodiment can be used to deliver very labile drugs which have very limited shelf-lives or short biological half-lives whereupon the activator (third phase) can be added just prior to intravascular administration such that the inactive drug becomes activated after the microcapsules have reached the target site. Upon activation, the microcapsules are exposed to an electromagnetic field effective to heat the magnetic particles, thus melting the polymer shell and releasing the activated drug. This can maximize the therapeutic effectiveness of the short-lived drug at the target site of action.

One or more of the phases of the microcapsule of the invention may further comprise fluorescent molecules selected from the group of fluorescent molecules consisting of fluoresceins, cyanins, naturally fluorescent molecules, and rhodamines, and others excited between 260 and 700 nanometers. This is particularly useful where radiocontrast media are not desirable or where an additional tracking method is useful or where it is of value to monitor the presence or absence of a layer in the microcapsule, fluorescent molecules may be incorporated into the microcapsule of the invention. Thus, for instance, as described more fully below, it may be useful to incorporate a hydrophilic fluorescent molecule in the aqueous liquid in order to determine the relative location and number of aqueous liquid layers in a certain production batch of microcapsules produced by the methods of the invention.

Critical to the success of the methods of the invention is the substantial limitation of mixing between said phases to diffusion-driven convection and low fluid shear (preferably less than 50 dynes/cm$^2$). One manner in which to so limit other types of mixing is to carry out the methods under microgravity. Microgravity is defined as a gravity force of less than $1\times10^{-3}\times$g. Such gravitational environments may be achieved in a variety of ways, at least some of which are detailed herein. For instance, microgravity may be achieved in certain trajectories of sounding rockets. Even longer periods of microgravity may be obtained with temporary orbiters such as the space shuttle. Relatively indefinite periods of microgravity may be obtained in permanent or semipermanent orbital space craft such as the orbital space station and other geosynchronous orbital satellites. The exposure of the first and second liquids to microgravity has been found to be effective in forming the microcapsules of the invention where the exposure is at least 6.5 minutes in duration, and later studies have shown that a few seconds is sufficient. Certainly, as described more fully below, greater exposure periods have also been proven successful. The inventors have shown that periods of exposure as short as a few seconds will also produce adequate numbers of microcapsules.

In formation of microcapsules, however, the methods of the invention will not necessarily use microgravity in order to limit mixing between the phases. Of course, such limitations of mixing can be promoted by carrying out the methods below ambient temperature. Limitation of interactions between the phases is best promoted by substantially balancing the specific gravity between said phases as is described below. The formulations and methods necessary to achieve Earth-normal microcapsule formation are described in greater detail herein. In either case, or in combinations of these techniques, mixing between the two phases may be chiefly the result of diffusion-driven convection.

The inventors have found that there is a greater size distribution which results from microencapsulation at Earth-normal gravity. At least a partial reason for this wider size distribution is apparently the inability under Earth-normal gravity to avoid certain sedimentation phenomena alone and sedimentation effects combined with weight-related contact of sedimented microcapsules. These facts require some additional manipulation under Earth-normal environments not required in the 0-g environments—namely, sieving of the resulting microcapsules in order to generate more uniform fractions. Therefore, at Earth-normal gravity, the utility of the outer coating of the microcapsules of the present invention become even more important. Enhancing the ruggedness of the Earth-normal microcapsules by curing and other steps as related herein may also be used.

A preferred method of making a multi-layered microcapsule comprises: formulating a first phase comprising an organic solvent selected from the group of organic solvents consisting of ethyl alcohol, methyl alcohol and isopropyl alcohol, a first polymer soluble in the first phase selected from the group of polymers consisting of glycerol monosterate, glycerol monooleate, glycerol monolaurate, glycerol dioleate, glycerol disterate, cholesterol, stigmasterol, phytosterol, campesterol, lecithins such as phosphatidyl cholines (e.g., Centrolex-F®), a co-solvent selected from the group of co-solvents consisting of $C_3$-$C_8$ alcohols, tetrahydrofuran, dioxane, acetonitrile, dimethylformamide, dimethylacetamide, and dimethyl sulfoxide, an oil selected from the group of oils consisting of poppy seed oil, olive oil, peanut oil, sesame oil, cotton seed oil, soybean oil, safflower oil, corn oil, sunflower seed oil, canola oil (unsaturated oils), or mineral oil, long chain paraffinic oil, and liquid petrolatum (saturated oils), and water; formulating a second phase immiscible with the first phase, the second phase comprising water, a second polymer soluble in the second phase selected from the group of polymers consisting of polyethyleneglycol 1000-8000 daltons, dextran 1000-10000 daltons, polyvinylpyrrolidone, polyvinyl alcohols, gelatin, gum tragacanth, carrageenan, Karaya gum, Guar gum, gum arabic, alginates, carboxymethyl cellulose, hydroxypropyl cellulose, hydroxyethyl cellulose, carboxypropyl cellulose, lecithins, a surface active agent selected from the group consisting of sorbitan monooleate treated with ethylene oxide, dextran, polyethylene glycol, $C_{12}$-$C_{20}$ fatty acids, cyclodextrins, PEG dextran copolymer, PEG acrylates, lactides, galactides, chitosan, Zein®, carbapol, polyoxamers, quaternary ammonium salts, and a salt selected from the group of salts consisting of NaCl, KCl, $CaCl_2$, $MgCl_2$, quaternary ammonium salts, such as cetyl trimethylammonium bromide, 2-amino-2-methyl-1-propyl aminomethyl propanol, and 4-methoxy-4(3-phosphatidyl choline)spiro(1,2-dioxetane-3-g,1-adamantane) disodium salt; the surface active agent having a hydrophilic/lipophilic balance value greater than that of the first polymer; the second polymer having a hydrophilic/lipophilic balance value lower than that of the surface active agent; creating an interface between the first and second phases in a manner that substantially limits fluid shear; and, substantially maintaining adsorptive surface characteristics of said interface.

Microcapsule products produced by any of the methods of the invention are also claimed. The methods of the invention are used to form unique multi-lamellar, microcapsules, having alternating hydrophilic and hydrophobic liquid layers surrounded by a flexible, semi-permeable, polymeric outer "skin". The outer skin which can be either hydrophilic or hydrophobic, is designed to allow controlled drug diffusion out of the microcapsule. The outer skin is also designed to have a melting temperature below the Curie point of the encapsulated magnetic particles, so that exposure to an electromagnetic field will cause the melting of a hole or pore in the skin, thus aiding in release or diffusion of dissolved chemicals out of the microcapsule.

Unlike any natural phospholipid or other component of cell membranes, the outer skin of the microcapsules of the invention will not reform an intact membrane, and is designed to avoid recognition and phagocytosis by immune cells, thereby increasing the amount of drug delivered to the tissues. The multi-layered microcapsules of the invention can entrap multiple drugs in different solvent compartments and saturated solutions of drugs which may then form crystals inside the microcapsule. Radiocontrast medium can be co-encapsulated with drugs in the same microcapsule. A magnetic resonance contrast agent can also be encapsulated such as various metallo-organic compounds including aqueous soluble ferrous gluconate, Gadolinium diethylene triamine pentaacetic acid and hydrocarbon-soluble, iron pentacarbonyl.

The microcapsules of the invention have been found to provide a surprisingly uniform distribution of diameters. This uniformity is particularly important in its medical applications. The microcapsules thus produced can be used to deliver several drugs which can be released sequentially to the target tissues through choosing magnetic particles with various Curie points, for example. The deformable, liquid-filled microcapsules also have advantages over solid matrix microcapsules in achieving maximum packing density in blood vessels, thereby decreasing blood flow to target tissues. This enhances the therapeutic effect of combined drug delivery and reducing the blood supply to vascular tumors (chemoembolization).

The methods of the invention result in more spherical, uniform size distributions of microcapsules. When comparing certain prior art equipment and methods for forming microcapsules (Microfluidics, Inc.), the inventors found that even the preferred formulations disclosed herein were incapable of providing such uniformity with the prior art equipment. In certain instances, hardly any microcapsules formed at all where mixing and vortexing were used to distribute one phase into the next. In others, poorly formed and non-spherical microcapsules resulted. In contrast to the failures of the prior art methods, the methods of the invention were successfully used to generate uniform, spherical microcapsules both under unit gravity and under microgravity conditions. Such uniformity enables superior drug delivery. Enhanced uniformity also enables better dose distribution calculations for establishing the therapeutic dose in the treatment of specific diseases, especially treatment of certain types of tumors. Importantly, the methods of the invention allow the formation of larger-sized, multi-lamellar microcapsules (1-350 micron) than heretofore possible. Such a capability allows multilamellar microcapsules to be made specifically for inhalation and deposition in the lungs. This uniformity allows facile sieving or filtering of the microcapsule products in order to obtain highly uniform diameter fractions.

Most liposomes have a very small hydrophobic compartment and therefore can only carry small amounts of hydrophobic drugs. Contrastingly, the microcapsules of the invention have a relatively large hydrophobic liquid compartment which enables delivery of more hydrophobic drug per microcapsule. Moreover, the microcapsules of the invention have relatively large hydrophilic and hydrophobic compartments which permits tandem delivery of both water soluble and non-water soluble drugs in the same microcapsule.

As previously noted, the microcapsules of the invention may contain polysaccharides. Inclusion of such polysaccharides is one of several aspects of the methods of the invention that enhance the formation of the microcapsules. The inclusion of injectable polysaccharides in the formulations of the invention contributes to the driving forces that control phase separation and phase partitioning of the entrapped drugs. The polysaccharides also provide increased shelf-life and stability of the parenteral suspensions. Use of the neutral salt solutions in the aqueous phase enhances micelle formation, lateral phase separation, and increases the dispersion of microcapsules and their stability as they are formed. In certain embodiments, phosphate buffered saline containing dextran may be used.

The methods of the invention, in certain embodiments, utilize a non-phospholipid outer coating. The microcapsules formed by this method are contained in a thin, semi-permeable, outer membrane comprised of hydrophobic (e.g. mono- or polyglycerides or waxy-polymers) or hydrophilic polymers (e.g., PVA or PVP), depending on the desired diffusion release rate of the encapsulated drug. Thus, the coating has the advantage of allowing design of the appropriate drug diffusion and release characteristics while avoiding certain of the disadvantages of conventional liposomes (and lipid bilayers). In particular, the coating produced by the methods of the invention around the outer surface of the microcapsule avoids being readily detected and largely eliminated by the reticuloendothelial system (RES). The outer skin protects the microcapsules against shear forces encountered during manufacturing processes and during transport within the vascular system en route to the target tissues. The hydrophobic outer membrane also can be designed to retard oxygen transport, thereby reducing oxidative degradation of the entrapped drug and improving the shelf-life of the parenteral suspensions. The flexible/deformable outer skin on the microcapsules of the invention results in increased packing densities within vascular beds. This results in microcapsules superior to solid microspheres (e.g. gelatin, albumin or starch) commonly used for chemoembolization therapy against tumors. The formulations used to produce the microcapsules of the invention are summarized below.

TABLE 1

Formulas for Primary, Secondary and Tertiary Solutions for Microencapsulation

| | | Primary Solution (also can contain drug) | Secondary Solution | Tertiary Solution (also can contain dissolved drug) |
|---|---|---|---|---|
| Group 1 | | First Solvent (75-90%)<br>  ethyl alcohol<br>  methyl alcohol<br>  isopropyl alcohol<br>Organic Co-solvent 0-20%<br>  $C_4$-$C_8$ alcohols<br>    tetrahydrofuran (THF)<br>    dioxane<br>    acetonitrile<br>    dimethylformamide (DMF)<br>    dimethyl sulfoxide (DMSO)<br>Polymers<br>(1-5%) (monoglycerated)<br>    glycerol monostearate<br>    glycerol monooleate<br>    glycerol monolaurate<br>(polyglycerides)<br>    glycerol dioleate<br>    glycerol distearate<br>(sterols)<br>    cholesterol<br>    plant sterols—<br>      stigmasterol<br>      phytosterol<br>      campesterol<br>(phospholipids)<br>    lecithins<br>    e.g., phosphatydl choline<br>    (Centrolex-F□)<br>Water (1-5%) water<br>Oils<br>(unsaturated or saturated)<br>(1-10%)<br>    iodinated poppy seed oil<br>    (IPO)<br>      mineral oil<br>      cotton seed oil<br>      olive oil<br>      safflower oil<br>      canola oil<br>      peanut oil<br>      sesame oil<br>      corn oil<br>Dissolved Drugs<br>(1% to saturation) | Second Solvent water<br>(70-98%)<br>Polymers<br>(1-10%)<br>    polyethylene glycol<br>    PEG - 400-20000<br>    (polysaccharides)<br>    Dextran 4000-20000<br>    (range 1000-100,000))<br>    others<br>      polyvinyl-<br>      pyrrolidone<br>      polyvinyl alcohols<br>Surfactants<br>(ionic and non-ionic)<br>(1-4%)<br>    sorbitan<br>      monooleate plus<br>      ethylene oxides<br>    Dextran<br>    PEG<br>    $C_{12}$-$C_{20}$ fatty acid<br>      quaternary $NH_4$<br>      salt<br>Additional Polymers<br>(1-10%)<br>(hydrocolloids)<br>    gelatin<br>    gum tragacanth<br>    carrageenans<br>    karaya gum<br>    guar<br>    gum<br>    alginates<br>    (celluloses)<br>      celluloses<br>      (CMC, WEC,<br>      HPC)<br>Salts<br>(0.01-3%)<br>    NaCl KCl,<br>    $CaCl_2$, quaternary $NH_4$<br>    salts,<br>    cetyl<br>    PPD<br>Dissolved Drugs<br>(1% to saturation)<br>therapeutic of choice | Oils (up to 100%)<br>  IPO<br>  heavy mineral oil<br>  olive oil<br>  same as in<br>    primary soln.<br>  Paraffins<br>    ($C_{20}$-$C_{38}$)<br>Alternative<br>Aqueous solutions containing—<br>  Immunoglobulins<br>  Albumin<br>  Gelatin<br>  Hydrocolloids<br>  plant sterols<br>  phospholipids<br>  polysaccharides<br>    starches<br>    cyclodextrins<br>Polymers<br>Surfactants (1-4%)<br>(ionic and non-ionic)<br>  long chain<br>  celluloses<br>Additional Polymers<br>Same as secondary solution<br>Dissolved Drugs<br>(1% to saturation)<br>  soluble therapeutic |
| Group 2 | | Aqueous First Solvent water<br>(70-90%)<br>Co-solvents (0-20%) | Same as<br>Group 1<br>Co-Solvents | Oils (up to 100%)<br>Same as Group 1<br>Alternatives |

TABLE 1-continued

Formulas for Primary, Secondary and Tertiary Solutions for Microencapsulation

| Primary Solution (also can contain drug) | Secondary Solution | Tertiary Solution (also can contain dissolved drug) |
|---|---|---|
| $C_3$-$C_8$ alcohols | Same as primary solution | Aqueous solutions |
| tetrahydrofuran (THF) | Polymers (1-10%) | Same as Group 1 |
| dioxane | Same as Group 1 | Polymers |
| acetonitrile | Surfactants (1-20%) | Same as Secondary Solution |
| dimethylformamide (DMF) | (ionic and non-ionic) | Surfactants |
| dimethyl sulfoxide (DMSO) | Same as Group 1 | Same as Secondary Solution |
| Polymers hydrophilic | Additional Polymers 1-10% | Dissolved Drugs |
| (water soluble) | Salts (0-3%) | 1% to saturation |
| polyvinylpyrrolidone (PVP) | Same as Group 1 | |
| polyvinyl alcohols (PVA) | Dissolved Drugs | |
| hydrocolloids | 1% to saturation | |
|   gelatin | | |
|   gum tragacanth | | |
|   carrageenans | | |
|   karaya gum | | |
|   guar gum | | |
| alginates | | |
| celluloses CMC, CPC | | |
| phospholipids | | |
|   lecithins | | |
|     phosphatydl choline | | |
|     Centrolex F | | |
| polysaccharides | | |
|   corn starch | | |
|   cyclodextrins | | |
| Oils (unsaturated or saturated) 1-10% | | |
|   iodinated poppy seed oil (IPO) | | |
|   mineral oil | | |
|   cotton seed oil | | |
|   olive oil | | |
|   safflower oil | | |
|   canola oil | | |
|   peanut oil | | |
|   sesame oil | | |
|   corn oil | | |
| Dissolved Drugs | | |
| 1% to saturation | | |

Where the microcapsules of the invention comprise a pharmaceutical composition, certain medically related advantages may be obtained. Thus, due to the uniformity and ease with which the methods of the invention allow formation of multilamellar microcapsules, co-encapsulation of multiple drugs is made possible. Thus, for instance, as will be described more fully below, co-encapsulation of drugs and radiocontrast medium in the same microcapsules is made possible by the methods of the invention. Such co-encapsulation allows radiological monitoring of the tissue distribution during intravascular delivery. Additionally, incorporation of fluorescent-labels for entrapped drugs enables accurate measure of the drug compartment volumes (using fluorescent imaging techniques) and convenient determinations of the drug loading efficiencies, particle size distributions and measurement of shelf-life stability of the final parenteral suspensions. In some applications made possible by the methods and compositions of the invention, the organic phase can include a tracer compound or radiocontrast medium to provide the additional advantage of real-time imaging of the microcapsules with computerized tomography (CT) scanning as they are released from the catheter en route to the target tissue. Other examples include aqueous soluble metallo-organic compounds used for diagnostic imaging such as ferrous gluconate or Gadolinium diethylene triamine pentaacetic acid (Gd-DTPA) used for nuclear magnetic resonance imaging and hydrocarbon soluble agents such as iron pentacarbonyl which also may be used for NMR imaging.

Production of multi-layered microcapsules via the methods of the invention which possess alternating hydrophobic and hydrophilic drug compartments allows for design of multiple-therapy microcapsules. Spontaneous formation of microcapsules with one or more large hydrophobic solvent compartments increases the potential application for delivery of more aqueous-insoluble drug at target sites with adequate vascular networks. By using the microcapsules made possible by the methods of the invention, sequential diffusion of two or more drugs out of the same microcapsule may be achieved at the target tissues. The incorporation of aqueous-soluble cyclodextrin which can act as an internal hydrophobic drug carrier is also made practical using the single step methods and formulations provided in this disclosure. This extends the capability of the invention in delivering otherwise aqueous-insoluble drugs.

For instance, the use of multiple drugs within the same microcapsule provides microcapsules specifically designed for chemoembolization treatments. Multiple-drug microcapsules also may be used to deliver first a chemotherapeutic drug which kills tumor cells, and then an immuno-adjuvant (tumor necrosis factor) or immunological stimulant (e.g.

interferon-g) that would enhance the patient's immune response to the tumor. Multiple-drug microcapsules can also be used to deliver combinations of chemotherapeutic drugs to tumors that are located in privileged sites, such as brain tumors. For example, and as described more fully in the examples to follow, simultaneous delivery of different types of drugs in the same microcapsule is made possible with the methods and compositions of the invention, e.g. diaziquone and cis-platinum to brain tumors via the carotid artery [Kimier et al. 1993]. Multi-layered microcapsules may also be used to treat deep infections that are resistant to systemic antibiotics. In these applications, one or more antibiotics may be sequentially delivered to the site of the infection. Multi-layered microcapsules can be designed to protect active forms of urokinase and other thrombolytic enzymes until they are delivered and entrapped at the local site of a blood clot, where therapeutic doses of the enzyme may then be released by lysing the outer membrane to dissolve the unwanted embolism. The multilamellar microcapsules can also be used to deliver immunostimulants; cytokines such as Interferons, Interleukins, and growth factors; antinauseants such as metoclopramide and tetrahydrocannabinol; multiple fibrinolytic enzymes such as urokinase (uPA), tissue plasminogen activator (tPA) and streptokinase; steroids such as hydrocortisone, dexamethasone, etc.; anti-fungals such as nystatin and griseofulvin, anti-virals such as amantidine, iododeoxyuridine, riboviran; and multiple antibiotics such as amoxicillin, ampicillin, etc.

In one embodiment, as related to the space-based research that lead to the Earth-normal embodiments of the invention, exposure to microgravity for at least 20 seconds in duration produced microcapsules. If the microcapsules of the invention are to be used in 1-g environments, as is generally anticipated, an additional step comprising recovering the multilayer microcapsules will be necessarily accomplished at Earth-normal gravity. Generally, this step will be accomplished by reentry and recovery of the orbital device by which exposure to 0-g was accomplished. While it is preferred to accomplish the recovery without exposure of the formed microcapsules to physical extremes (pressure, temperature, shearing, mixing, etc.), recovery of the microcapsules of the invention have been accomplished via a transition from microgravity to Earth-normal gravity at accelerations of at least 15-g without substantial loss of integrity.

As used herein the term contain or contained in a microcapsule or in a liquid phase or layer is construed to have its normal meaning, and may include suspended or dissolved as in a liquid layer, or interface, and also includes the meaning associated with a polymer shell including on its inner or outer surfaces. As used herein, the term "prodrug" or "proenzyme" includes the meaning of a precursor, such as intraglandular prohormones, or the meaning of an agent whose drug or enzymatic activity, or pharmacological action, results from a conversion or transformation into an active or more active form. Such conversion may be the result of a metabolic process or biotransformation, or it may be the result of an artificial reaction.

BRIEF DESCRIPTION OF THE DRAWINGS

For a detailed description of a preferred embodiment of the invention, reference will now be made to the accompanying drawings wherein.

DETAILED DESCRIPTION OF THE PREFERRED EMBODIMENTS

Figure 1A:
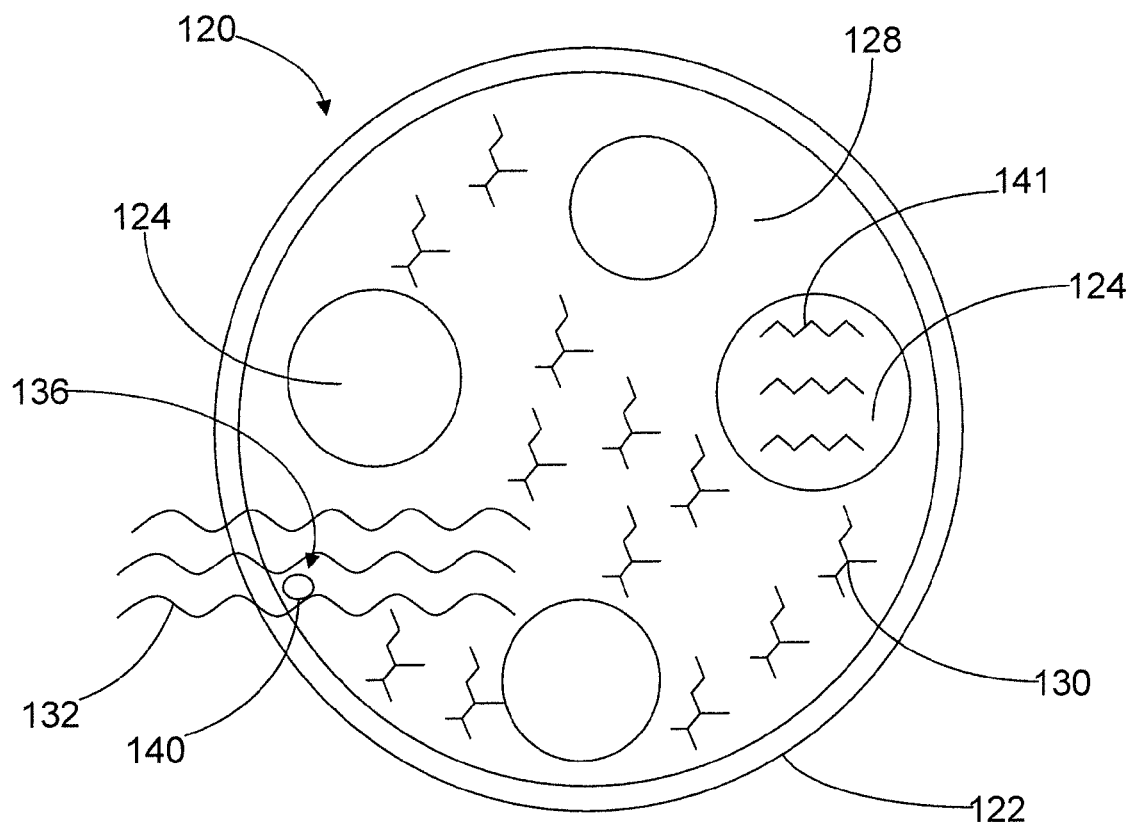
FIG. 1A Schematic of microcapsules containing magnetic particle that is heated by exposure to an electromagnetic field.

The present disclosure is drawn to multi-layered microcapsules and methods of making microcapsules having a polymeric outer membrane that may enclose immiscible liquid phases that contain drugs or bioactive chemicals and magnetic solid particles that can absorb electromagnetic energy and thereby heat up to a predetermined temperature (Curie point or Curie temperature), which is sufficient to melt a hole in, or to melt at least a portion of, or otherwise lyse the polymeric shell and release the liquid contents of the microcapsule including the drug or bioactive chemical. The microcapsules described herein may, in certain embodiments be injected into arteries leading to thrombi, vascularized tumors, or other capillary beds, or they may be injected directly into tumors or other tissues in order to reach a target site. When the microcapsules are at the target site, the patient or subject may be exposed to an external, or internal electromagnetic field, typically for a period of a few minutes, thereby causing the magnetic particles to reach their Curie temperature and melt the polymeric shell and release the drug at the target site. In certain embodiments, multiple releases of drug may be achieved by including microcapsules containing magnetic particles with differing Curie points. In addition, these microcapsules may also contain different drugs so that sequential administrations of a combination of drugs may be achieved by manipulating the frequency of the external field and the length of exposure. The use of magnetic particles for controlled drug delivery may be used with any of the microcapsules and delivery methods as described herein and in related applications.

The microcapsules described herein provide advantages over prior compositions and methods in that the microcapsules may be designed to that the Curie temperature is from about 41° C. to any temperature, even as high as 95° C. without causing widespread thermal damage to local tissues. Based on the small size relative to a cell and the small number of particles, collateral damage will be minimal. In addition, the microcapsules may be used to deliver multiple drugs from a single administration, or to release several pulses of drug as the case may be. Another advantage is that the drug releases are triggered by external electromagnetic fields that are non-invasive, can be applied for a shorter time than is necessary for tissue hyperthermia, and do not rely on local hyperthermia, which is hard to control and may cause collateral damage. In addition, induction heating of the magnetic particles is not restricted to frequencies and power densities normally needed to induce hyperthermia. The microcapsules are also useful for storing unstable drugs for extended periods, possibly in an inactive form, and for carrying drugs or bioactive agents to the target site in a protected environment until they are released, thus avoiding unwanted drug activity at non-specific sites, as well as avoiding potential problems with an immune response to the agent. Finally, the microcapsules containing magnetic particles can be separated and purified using DC magnetic fields and routine separation techniques, and they can be concentrated in a chosen tissue location by application of an external magnetic field.

For those embodiments described herein in which an electromagnetic field is used to heat microparticles, field strength may be described alternatively as typically on the order of 85-95 KHz or 1500-2400 A/m, or as approximately 3-5 KW. It is known that microparticles and microcapsules may be made to absorb other types of energy than an electromagnetic field. In certain embodiments the microcapsules may contain microparticles or internal components that specifically absorb radiofrequency (6.7-27.1 MHz) or 915-2450 MHz microwave radiation, or ultrasonic waves at greater than 18 KHz, such that the microparticles or internal components are heated to a temperature above the melting temperature of the outer membrane. More specifically, the microcapsules are designed so that, for a particular type of energy to be used (e.g., electromagnetic, radiofrequency, microwave or ultrasound), the specific absorption rate (SAR) of a microparticle or internal component is much greater than the SAR of the outer membrane, which is much greater than the SAR of the surrounding tissue. The design of such microcapsules is described in more detail in the Examples below.

The present disclosure provides methods of encapsulating multiple drugs or biological therapeutics into liquid microcapsules or liposomes that are designed for delivery to selected tissues or organs where, upon activation, a short-lived drug can be released directly to the target area by diffusion out of the microcapsules. A method of the present disclosure may be used to form multi-lamellar microcapsules having alternating hydrophilic and hydrophobic liquid layers surrounded by a flexible, semi-permeable, polymeric outer "skin." In this embodiment, the outer skin is designed to allow sustained diffusion of the bioactive drug from the microcapsule.

The methods and compositions of the present invention may use special formulations of solubilized drugs, surfactants, polymeric co-surfactants, and energy absorbing components within a specific immiscible liquid phase. The energy absorbing medium (e.g. photo activator, thermoabsorber, etc.) absorbs electromagnetic, ultraviolet (UV), infrared (IR), ultrasonic, radiofrequency (RF), or microwave radiation and thereby causes chemical activation of a chemical substrate or drug precursor into a bioactive drug molecule which can readily diffuse out of the microcapsule. The absorbed energy also can be used to create thermal convection, Maragoni flows or other high velocity flows that can cause interfacial mixing, redistribution of partitioning compartments within immiscible phases, and increased radiocontrast of selected components within certain liquid compartments. This is exemplified by UV (220-390 nanometers) photoactivation of microcapsules containing drugs, fluorescent compounds and radiocontrast media in the same microcapsule. The in situ activated microcapsules are characterized by: outer polymeric membranes that are both transparent to the activating radiations and are permeable to the bioactive drug thereby allowing sustained time-release of the active drug; immiscible fluid compartments inside the microcapsules or internal spheroids surrounded by thermosensitive or a shear sensitive interfacial boundary or membrane, containing chemical components that absorb the activating energy; chemical reactions or convective mixing that convert the prodrug or proenzyme to the bioactive form or change the molecular form of a drug (which is already bioactive) to increase its diffusion rate out of the microcapsule or its bioavailability once it has been released; and a longer shelf-life than that of the bioactive drug dissolved or suspended in the carrier solution. In the practice of the invention, one may expose the microcapsules to a first form of energy or wavelength in order to cause mixing of immiscible layers or to otherwise activate a prodrug or chemical agent, and subsequently expose the microcapsules to an electromagnetic field designed to heat the microparticles and release the contents of the microcapsules.

Included within the present disclosure are multi-layered liquid microcapsules and methods of forming the multi-layered liquid microcapsules comprising a drug permeable outer skin or membrane surrounding a sphere of immiscible fluid compartments. The immiscible compartments may contain a drug precursor in one phase and an activating agent in another phase. The activating agent may be activated by exposure to external electromagnetic radiation or other forms of activating energy causing it to react with the drug precursor to produce an active drug or agent.

Embodiments of the present invention include methods of exposing the microcapsules to activating radiation or other forms of activating energy. These methods include, but are not limited to the following:

Direct exposure of the microcapsules in dry or liquid dispersion just prior to dispensing. This method may be accomplished, for example, by exposure to radiation from a band pass filter system, laser light, infrared light, radio waves or microwaves, or a combination of same, all of which are transmitted through the outer membrane of the microcapsules to be absorbed by the activating agent which has been co-encapsulated with the precursor drug.

Entrapment of the microcapsules in tissue followed by external administration of the activating energy through the skin and outer tissues of a subject without physiological damage and absorption of the energy by the activating agent within the microcapsules, or by magnetic particles resulting in heating and melting of the polymer outer membrane.

Entrapment of microcapsules in arterioles, venules, or tissues, followed by exposure of the microcapsules via intravascular catheters, or other internal devices containing a fiber optic probe, electromagnetic transducer, or other miniature energy transducer that can transmit the activating energy locally to the entrapped microcapsules, again followed by heating of the magnetic particles to release the activated contents.

In the practice of certain embodiments of the inventions, the absorption of the activating energy may result in a chemical reaction between an activator and a prodrug or enzyme precursor that produces a bioactive molecular moiety, or such absorption may drive fluid mixing and turbulent fluid flows wherein the internal mixing of the immiscible internal phase containing the prodrug and the internal phase containing the activator results in production of the bioactive form of the drug. Alternatively, absorption of activating energy may occur inside inner spheroids surrounded by a thermosensitive membrane containing a solution of the activating agent where energy deposition increases the temperature in the spheroid causing the thermosensitive membrane to rupture or dissolve, allowing the activating solution to mix with the next outer solution containing the prodrug or substrate to produce the active agent. Such mixing may also be caused by ultrasonic radiation, which would be effective to lyse the inner spheroids. The activating energy may also be absorbed by the outer membrane of the microcapsules, to produce an agent such as free radicals, superoxides, oxidizing or reducing agents to activate a prodrug.

An embodiment of the present invention is also microcapsules in which activating energy is absorbed by radiocontrast media contained in the microcapsules, thus increasing the radio-opacity of the media while the microcapsules are trapped in tissue. Examples of such radiocontrast media include, but are not limited to halogenated oils such as halogenated poppy seed oil, cotton seed oil, soybean oil, safflower oil, corn oil, sesame seed oil, canola oil, and others that can be readily iodinated to produce a radio-opaque contrast medium for radiographic imaging.

For the purposes of this disclosure, the terms "a", "an" and "one" encompass the conventional meaning, and includes the meaning "one or more." Hence, a description of a microcapsule, or a pro-drug, for example, would include the meaning one, or one or more, as a particular context requires.

Thermoparticle Temperature Regulation

At high frequencies, the heating of ferromagnetic metal rods or particles by electromagnetic induction is mainly due to eddy currents that are known to circulate almost exclusively in a thin surface layer. Under such conditions, the power into the thermoparticles per unit length in an alternating magnetic field, which is applied parallel to the long axis, is:

$$P_e = \pi(\mu_0 \mu \rho f)^{1/2} aH^2$$

where $P_e$ is the power input due to eddy currents, W/m; $\mu_0$ is the permeability of free space, $4\pi \times 10^{-7}$ Wb/A·m; $\mu$ is the relative permeability of the thermoparticle, dimensionless; $\rho$ is the electrical resistivity, ohm·m; a is the radius of the thermoparticle, m; H is the amplitude of the sinusoidally, varying magnetic field, A·m; and f is the frequency, $s^{-1}$ (Chen et al., 1988). From this equation, the only material properties that affect the power input to a heating thermoparticle are $\mu$ and $\rho$; H and f are characteristics of the induction heating equipment and its operating conditions. Resistivity does not change appreciably at the Curie temperature, and the variation of resistivity in the temperature range just below the Curie temperature is small compared to the corresponding change in permeability. More importantly there is a drastic reduction in the relative permeability as the temperature closely approaches the Curie temperature and this results in a corresponding reduction in the power absorption, current flow, and subsequent heating.

FIG. 1A is a schematic drawing of a drug or enzyme contained in a microcapsule that also contains a metal particle or sphere, such as a ferromagnetic ceramic particle, for example. The microcapsule 120 has an outer polymer membrane 122 that encloses one or more internal liquid phases 124, 128. In the embodiment shown in the figure, two internal liquid phases are shown. In the embodiment shown, a first internal phase 128 contains a drug or enzyme 130 for which the membrane 122 is impermeable. A second internal phase 124 may, in certain embodiments, contain an activating agent 141. A metal particle 136 contained in the microcapsule 120, has a Curie temperature higher than the melting point of the outer membrane 122. An activating electromagnetic field 132 is shown passing through the outer membrane 122 and causing the metal particle 136 to heat and to melt a hole or pore in the outer membrane 122. In various embodiments of the invention, the internal liquid layer adjacent the outer membrane 122 and that contains the magnetic particle 136 may be an aqueous layer or a hydrocarbon layer depending on the solubility of the active drug. The magnetic material used in microcapsules as described herein is also typically covered by a coating 140 such as a ceramic that is compatible with the liquids within the microcapsule and with the drug or active agent. Although the particles described herein are coated with ceramics, other coatings that are compatible with the liquid phases and drugs or solvents to be used in the microcapsules. Ceramics were chosen for the exemplary microcapsules described below because of their low antigenicity, they are not chemically reactive with the solvents or drugs used in the microcapsules, and the protect the metal from oxidation. Alternate coatings would include, but not be limited to methacrylates, alginates, dextran, polyacrylates, polyvinyl pyrrolidone (if the ferrous material is fully oxidized).

Figure 1B:
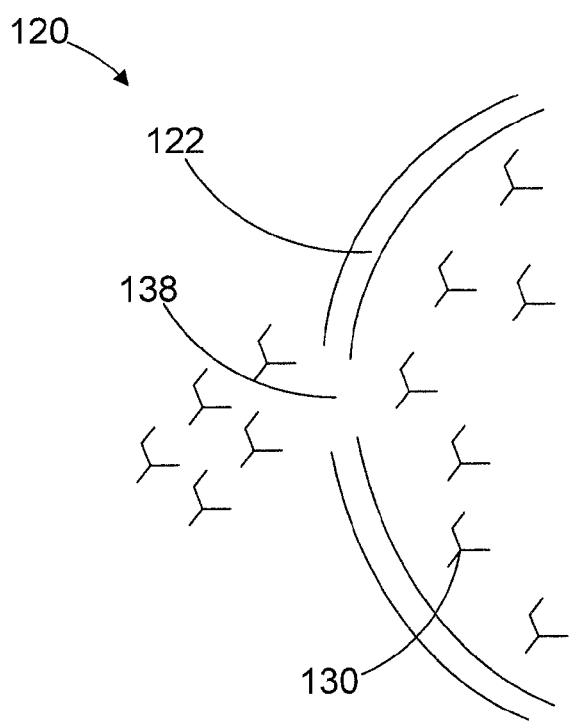
FIG. 1B Schematic of microcapsules after magnetic particle has melted a pore in the outer membrane and interior contents are diffusing from microcapsule.

FIG. 1B is a schematic drawing of a portion of a microcapsule shown in FIG. 1A after the metal particle 136 has melted a permanent hole or pore 138 in the outer membrane 122. The pore 138 allows the contents of the microcapsule 120 to leak out, including any drug 130 that is contained in an internal liquid phase 128 next to the outer membrane 122.

Figure 2:
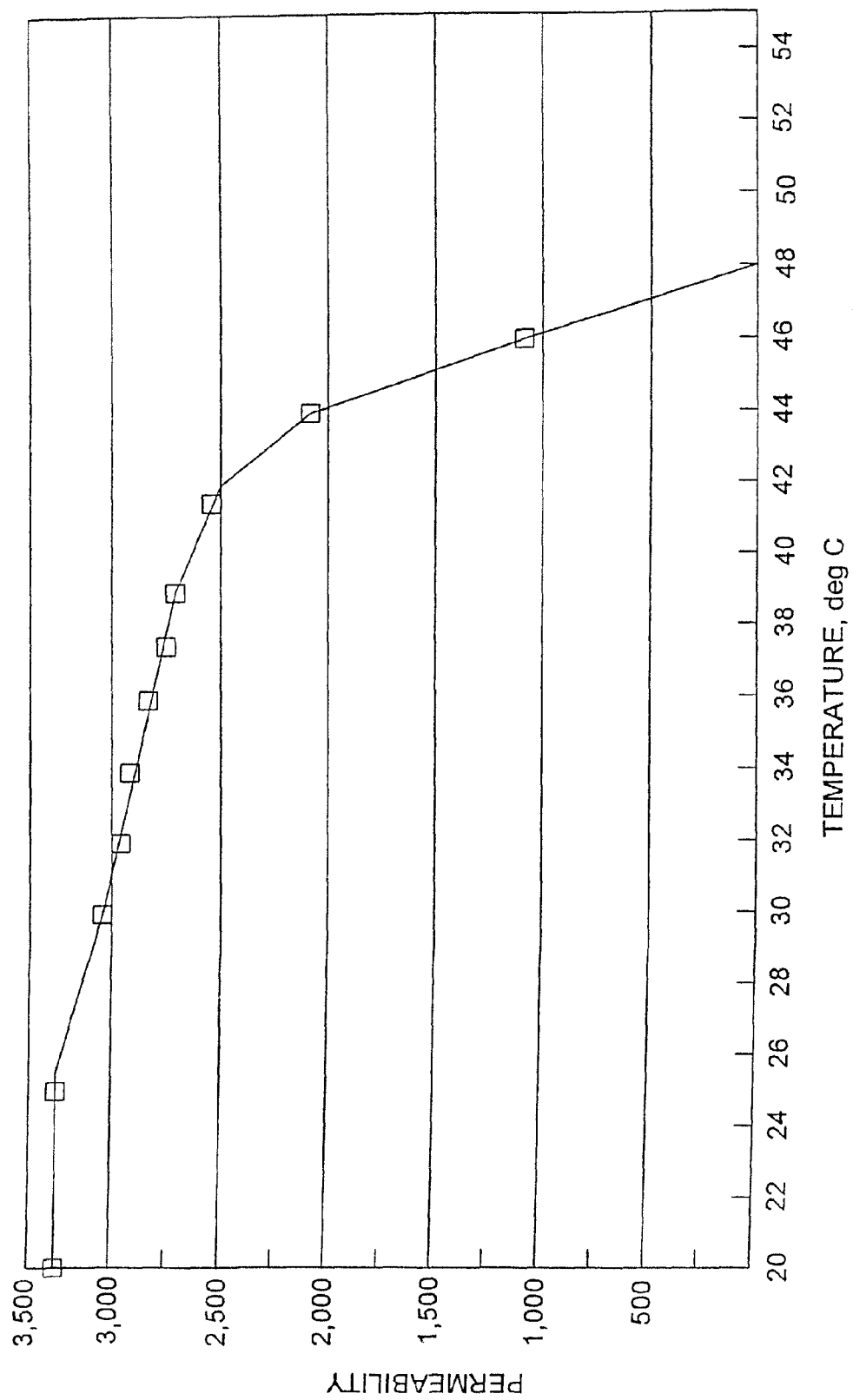
FIG. 2 Graph showing the permeability vs temperature of the ceramic ferromagnetic particles encapsulated in the microcapsules demonstrating a Curie temperature of about 48° C.

FIG. 2 is a graph showing the permeability vs temperature of the ceramic ferromagnetic particles encapsulated in the microcapsules described in Example XI. The Curie temperature is shown to be about 48° C.

A series of more than 38 separate experiments on four space flights has led to the development of aspects of this invention. These experiments along with their ground-based counterparts are described below for the purpose of pointing out the invention specifically and providing details useful in carrying out the invention. These specific examples, however, do not limit the scope of the claimed invention.

The following examples are offered by way of illustration and are not intended to limit the scope of the invention in any manner. All of the materials used in these examples were obtained from well known commercial sources, or as specifically stated in the examples. Essentially conventional methods were employed in each instance where no specific procedure is stated.

Example I

Microgravity Experiments Summary

The basic formulations and simplified liquid-liquid, dispersion methods were developed in 1988 and 1989. The basic concept is the formation of a multi-lamellar microcapsule with an aqueous drug/oil dispersion at its center, a hydrocarbon/oil drug#2 and/or radiocontrast medium (e.g. IPO) as a next layer, an aqueous layer/drug (e.g., cis-platinum) as a next layer, and a polymeric outer coating or skin. Microencapsulation-related experiments designed to overcome the limitations of the first methods were conducted on six space missions beginning in April 1989 with the Consort-I sounding rocket using the Materials Dispersion Apparatus (MDA) mini-lab developed by Instrumentation Technology Associates, Inc. The sounding rocket flights produced only 6.5 minutes of microgravity conditions, but this was adequate to form the unique microcapsules in a single step. Experiments on the Space Shuttle permitted 10 minute dispersion times followed by curing of the outer polyglyceride skin for eight days under microgravity conditions. A summary of these experiments is shown in Table 2. New formulations were tested on Shuttle STS-52, using only aqueous-soluble drugs, polymers and surfactants, and on STS-56 using alcohols as co-surfactants. The specific experiments and results are described in detail in the examples to follow.

TABLE 2

MED Flight Experiments Summary

| MISSION | DATE | EXPERIMENTS | MATERIALS | RESULTS |
| --- | --- | --- | --- | --- |
| Consort-1 | April 1989 | protein diffusion | urokinase & antibodies | diffusion rates established |
| Consort-1 | March 1990 | diffusion kinetics | urokinase & myoglobin | kinetics verified |

TABLE 2-continued

MED Flight Experiments Summary

| MISSION | DATE | EXPERIMENTS | MATERIALS | RESULTS |
| --- | --- | --- | --- | --- |
| Consort-4 | November 1991 | microencapsulation of drugs[a,b] | Cis-Platinum, amoxicillin, urokinase & Streptavidin | multi-lamellar microspheres w/ alternating hydrophilic & hydrophobic layers |
| Consort-5 | September 1992 | microencapsulation of drugs[a,b] | Cis-platinum, amoxicillin & urokinase | multi-lamellar microspheres w/ alternating hydrophilic & hydrophobic layers |
| STS-52 | October 1992 | microencapsulation of drugs (aqueous polymers only)[a,b] | Cis-platinum, amoxicillin & urokinase | multi-lamellar microspheres, crystals within microcapsules |
| STS-56 | April 1993 | microencapsulation of drugs (alcohol co-surfactants)[a,b] | Cis-platinum, amoxicillin & urokinase | multi-lamellar microspheres, crystals within microcapsules |

[a]Fluorescent labels included
[b]Fluorescent beads included

Example II

Gravity-Dependent Restrictions Recognized

Gravity-dependent restrictions in the basic liquid-liquid spontaneous microencapsulation process led to the design of several microgravity experiments to explore the utility of this process when density-driven phenomena were eliminated. In particular, density-driven, gravity-dependent restrictions of the liquid-liquid microencapsulation process were: early phase separation producing fragile microcapsules; interfacial dynamic flow causing coalescence of microcapsules. Failure of ground-based experiments to derive uniform microcapsules lead to a desire to attempt microcapsule formation in space.

The microgravity flight experiments led to the development of a new liquid-liquid microencapsulation process that involves use of surfactants and co-surfactants in the aqueous phase and co-surfactant alcohols in the organic phase, which also contained, in one embodiment, high molecular weight polymers that formed a tough outer "skin" on the final microcapsules. In microgravity, a single step dispersion produced unique multi-lamellar microcapsules containing various aqueous drugs co-encapsulated with iodinated poppy seed oil (a radiocontrast medium with a sp. gravity=1.35). Subsequent ground control experiments also produced some of these unique microcapsules and illustrated that the 1-g process could be improved to yield useable microcapsules by using different formulations. In particular, it became clear that the outer coatings substantially improved the ruggedness of the microcapsules formed.

Example III

Sounding Rocket Experiments

Initial experiments on Consort-1 and -3 were used to determine the effective mixing and diffusion kinetics in the MDAs (see below for apparatus description). This showed that sufficient volume was mixed at the interface via diffusion to allow formation of microcapsules. These experiments also provided the diffusion constants for each of the components of the liquid phases.

The first successful microencapsulation of drugs in microgravity was conducted on the Consort-4 mission in November 1991. The microcapsules were recovered and analyzed by microscopic image analysis. Mono-dispersed fluorescent beads were included as internal size standards and fluorescent labels were used to determine the distribution of drug in the various fluid compartments. Additional experiments, conducted on Consort-5 in September 1992, confirmed the capabilities of the new method for forming multi-lamellar microcapsules with alternating layers of hydrophilic and hydrophobic drugs.

Microcapsules formed in 38 microgravity mini-experiments used liquid-liquid dispersion of aqueous drug solutions, surfactant and polyethylene glycol dispersed in alcoholic co-surfactant solutions containing soluble polyglycerides.

Microcapsules of both oil/water and polymer/water/oil were recovered from the Consort flights. These experiments produced multi-lamellar liquid microcapsules (concentric spheres within spheres) comprised of three or more, alternating immiscible layers. Image analysis of the microcapsules was made possible by co-encapsulation of standard size fluorescent beads. Microcapsules were formed in the ranges of 1-15 microns, 40-50 microns, 110-130 microns and 160-230 microns in diameters. This was a substantial improvement over the prior art approaches which had initially been attempted by the inventors to derive microcapsules only in the 10 micron and less range. The size distribution covered a range of from about as low as 5 microns in diameter up to about 300 microns in diameter and greater. The average size of the microcapsules formed in these experiments was about 150 microns, greatly in excess of the average 10 micron or less diameters obtained with prior art approaches.

The ruggedness of the microcapsules formed under these conditions allowed for size segregation by filtration or other separation methods. Digital image analysis (National Institutes of Health image analysis program) of phase contrast and fluorescent images taken with a fluorescent microscope also confirmed that the aqueous-soluble drugs were routinely encapsulated within the inner aqueous core and the outermost aqueous shell of the microcapsules.

Multi-lamellar microcapsules were, also formed which contained relatively large amounts of IPO (Guerbet Laboratories—France, Savage Laboratories—U.S.A.) in discrete lamella, including microcapsules heavily loaded with IPO, which often comprises up to 38% of the total volume. Often small hemispheres of IPO were also found clinging to the outer surface of the large inner (aqueous) sphere or adhered to the outer polymer skin of the microcapsule.

Microcapsules formed by almost all of the formulations survived 15-g accelerations, severe vibrations and turbulent mixing, during the reentry of the experiment capsule, and have remained intact for two years after recovery from space.

These multi-layered microcapsules are similar to liquid-filled, thin-skinned, micro-balloons which are flexible enough to be manipulated on a microscope slide without collapse.

The microcapsules formed in just 6.5 minutes of microgravity retain their spherical shape and appear tough enough to survive the extensive physical manipulations required for sizing, final preparation and storage of parenteral suspensions, and the fluid shear encountered after intravascular injection. The inventors have also discovered that such capsules may form within a period of a few seconds.

Also formed were very unusual structures (multiple small spheres of aqueous-soluble drug) distributed within multi-lamellar o/w/o microcapsules, wherein the aqueous spheroids are arranged in an annular ring that appears fixed in a plane within the innermost sphere. These ring structures remain intact when the microcapsules are "rolled around" on the microscope slide without rupturing. These structures demonstrate the ability of the methods of the invention to form small spheroids that do not coalesce inside the larger microcapsule. Such structures may be advantageously used to control the specific volume to surface area ratio in order to control the rate of diffusion of a solute in such spheroids. In particular, sustained release of pharmaceuticals contained in such spheroids within microcapsules may find utility, as will applications in which the contents of such spheroids may be released into the microcapsule by ultrasonic irradiation.

Example IV

Space Shuttle Experiments

In experiments conducted on STS-52, the inventors co-encapsulated cis-platinum (diaminodichlor-cis-platinum; Bristol Laboratories) with IPO by forming microcapsules from water-soluble polymers using special formulations of aqueous, non-alcoholic solvents. Such formulations will find particular utility in co-encapsulations of anti-tumor compounds along with radiocontrast medium for tracking drugs in the body.

Polyvinyl pyrolidone (PVP), polyvinyl alcohol, and a commercial lecithin (Centrolex-F®; a phospholipid compound derived from soya and produced by U.S. Soya, Inc.) were used to form multi-lamellar microcapsules at 20° C. Fluorescent beads and fluorescent label were co-encapsulated with the drugs to permit drug-distribution measurements within the various lamellae, using fluorescence microscopy and digital image analysis. The final microcapsules were recovered and resuspended in either aqueous solutions, IPO or mineral oil. The microcapsules formed by these formulations were similar to those made using alcohol-soluble polyglycerides. However, without the hydrocarbon-soluble polymer membrane these microcapsules were more fragile and friable.

Another unique type of microcapsule was formed during these experiments that was characterized by drug crystals formed within the inner aqueous core of the multi-lamellar microcapsules. Microcapsules were formed which were packed (approximately 65% of the aqueous compartment) with crystals of Cis-platinum, an anti-tumor drug. Microcapsules containing crystals of amoxicillin were also formed in the STS-52 experiments. These illustrate that aqueous-soluble drugs can be encapsulated at very high concentrations near the solubility limit of the drug. After the microcapsules are formed the drug can become further concentrated (perhaps via the alcohol absorbing the water from the aqueous phase in which the pharmaceutical solute is dissolved) to form large crystals which are more stable than the dissolved drug during prolonged storage.

Microcapsules formed from first organic solvent/polymer methods appeared to be more rugged (by visual comparison under the microscope) than those formed on STS-52 formed from first solvent aqueous/polymer methods. The STS-56 experiments again produced multi-lamellar liquid microcapsules (multiple concentric spheres within spheres) comprised of alternating immiscible layers. Using fluorescent 6.4 micron beads and image analysis, it was found that the most interesting microcapsules were formed in the range of 10-15 micron, 40-50 micron, 50-100 micron, and 160-230 micron diameters. These diameter distributions were of particular interest since it is known that intraarterial uses can accommodate 50-300 micron diameter microcapsules while intravenous applications can only tolerate 1-10 micron microcapsules. Thus, by segregating the microcapsules into sized fractions (sieving), it is possible to address particular intravascular limitations.

As noted above, microcapsules were formed containing crystals of cis-Platinum or amoxicillin. The crystals apparently were formed after encapsulation. Several microcapsules were formed that contained a single, large cubic crystal of Cis-Platinum which so completely filled the inner sphere that only about 15% of the inner volume remained as a liquid. One encapsulated, cubic Cis-Platinum crystal was measured at 48 microns across within a 57 micron diameter microcapsule. After formation, some of the microcapsules were dispersed in an external oil phase (either IPO or mineral oil) and allowed to cure for eight days before return to Earth.

These microgravity experiments have shown that formation of multi-lamellar, alternating-phase microcapsules can be controlled by proper timed-sequence exposures of the immiscible phases using special solvent formulations and surfactants. Once formed, these microcapsules remain spherical due to the predominant surface tension of the internal phases and polymer/solvent phase partitioning at the interfaces.

These experiments clearly demonstrated the capability to use liquid-liquid diffusion mixing to form unique microcapsules containing hydrophilic and hydrophobic drugs under microgravity conditions. Thus, ground-based experiments were conducted to compliment and replicate the space experiments. These ground-based experiments were able to replicate the size range (5-250 microns in diameter) to a limited degree, but the average size microcapsule obtained was about 10-40 microns in diameter. Still, this was a substantial improvement over the prior art approaches which rarely formed microcapsules over 10 microns in diameter. It was also observed that the ground-based experiments resulted in less rugged microcapsules. This is likely a result of the gravity-dependent deformations of the spherical microcapsules as they form giving rise to areas of thinner polymer deposition. Thus, the flexible microcapsules, formed under micro-gravity conditions, were of more uniform size distributions than those formed in 1-g, were more rugged, and had a higher average diameter than ground-made microcapsules, largely due to the absence of thermal convection, buoyancy forces, and instabilities that occur at the immiscible interfaces. These problems have been largely overcome by new manufacturing apparatus as described in a related application, "Microencapsulation and Electrostatic Processing Device" invented by Dennis R. Morrison, Benjamin Mosier and John M. Cassanto, incorporated herein by reference.

The microgravity experiments illustrate the feasibility of co-encapsulating aqueous-soluble drugs, hydrocarbon-soluble drugs and oil-based contrast media within a lipid-soluble, polyglyceride outer film which cures rapidly enough to be impervious to oil or hydrocarbon resolubilization. They also allow the formation and harvesting of unique microcapsules which are durable enough to be removed from the external solvent without disruption or destruction of the internal phases. It is anticipated that these microcapsules will have several advantages over conventional liposomes that are designed for intravascular injection.

Example V

Flight Hardware Description

The microencapsulation experiments described herein were conducted using the Materials Dispersion Apparatus (MDA; ITA, Inc., Exton, Pa.). The MDA's consist of an upper and a lower block that contain chambers for each sample fluid. The blocks are misaligned at launch so that the chambers are not in contact with each other. Upon activation in microgravity, the blocks are moved to align the chambers so that the fluids can mix by liquid-liquid diffusion. Some of the experiments were conducted with a single-step fluid mixing, and some were done with a two-step fluid mixing technique which allows diffusion of a third fluid or sample into the mixture of the first two fluids while still in the microgravity environment. In these experiments, the shear forces are minimal while moving the fluids into contact with each other.

Example VI

Discussion and Alternative Embodiments

Spontaneous formation of multi-lamellar, microcapsules containing alternating layers of aqueous and hydrophobic solvent compartments is strongly dependent on the interfacial tension and the amount of mixing between immiscible liquid phases. On Earth this process is limited by gravity-dependent, density-driven separation of the immiscible liquids into stratified horizontal layers. In microgravity, this process is largely dependent on the surface-free energies of the different liquids, but independent of density-driven convection or buoyant phase separation. Hydrocarbon soluble, high molecular weight polymers have been included in the formulations to form flexible, permeable "skins" or outer coatings around the liquid microcapsules as they are created by phase partitioning mechanisms. It is also possible to form such polymer barriers between internal layers. The microcapsules can be formed and cured without deformation by contact with container walls.

More specifically, co-encapsulation of an aqueous-soluble, anti-tumor drug (Cis-platinum) and a radio-contrast medium (IPO), in microgravity, has produced a unique drug delivery system that can be visualized by radiologic or computerized tomography scanning to insure that the cytotoxic drug is delivered directly to the target tumor. Multi-layered microcapsules have been developed which can provide a new intravascular delivery system for targeted tissues and sequential, sustained and controlled release of multiple anti-tumor drugs. This method has resulted in formation of flexible spherical microcapsules of more uniform sizes, which can provide maximum packing densities and maximum drug delivery to target organs or tumors.

Multi-layered microcapsules can be designed to protect active forms of urokinase and other thrombolytic enzymes until they are delivered and entrapped at the local site of a blood clot, where therapeutic doses of the enzyme can diffuse out to dissolve the unwanted embolism. These immiscible-liquid diffusion methods also could be used for encapsulating certain labile drugs to make microcapsules for special purpose drug delivery systems, especially those designed to deliver drugs via the nasal or buccal mucosa or via inhalation directly to the lungs. Examples include protected delivery of mucolytic DNAse for sustained release treatment of cystic fibrosis and I anti-trypsin for patients with deficiencies in the lung epithelium.

Example VII

Redispersion of Microcapsules in Aqueous or Oil Vehicles

A frequently used second step includes dispersion of the microcapsules (after they have formed) in different aqueous/polymer solvents or in a pure oil phase. A unique attribute of microcapsules formed by these methods is that they do not re-dissolve in an oily external phase, even though the semipermeable outer skin is hydrophobic. This produces a suspension in the liquid carriers that are commonly used for intravascular administration.

Examples of suitable aqueous solutions for redispersion would include, but not be limited to dextran, PEG, phosphate buffered saline (PBS), Ringer's solution, or any solution known in the art that is selected so the membrane has little or no solubility in that medium. The solutions are sterilized prior to redispersion and are selected for the particular application, such as injection into a human. It is a further advantage, that redispersion in these solutions inhibits coalescence.

Example VIII

Exemplary First Organic Solvent Microcapsule Formulations

The following formulations have been used with particular success by the inventors in both Earth-normal and microgravity methods of making microcapsules.

Fluid 1—(hydrocarbon). The first solvent is a hydrocarbon fluid (ethyl alcohol, methyl alcohol, or isopropyl alcohol) with a low or medium HLB (HLB=5-10). One or more co-solvents are used (which also can act as co-surfactants). Small concentrations of oil and water are added. Into this mixture, the mono- or polyglyceride is dissolved up to 5% w/v.
An example is:
  88% IPA
  2.5% m-Hexanol
  2.5% n-Heptanol
  5% IPO
  2% $H_2O$
  5% GMS Fluid 2 (aqueous). The second solvent is water plus surfactants (ex. polyethoxylated sorbitan esters; polyethylene glycol). A polysaccharide (Dextran) and normal saline (0.9%) are added which helps achieve the desired critical micelle concentration. A pharmaceutical soluble in water is added.
An example is:
  1% PEG 4000
  5% Dextran-40 (MW=40,000)
  0.9% Sodium chloride
  2% Sorbitan Monooleate/20 moles Ethylene oxide
  Water (up to 100% volume)
  dissolved drug at specified concentration
  (according to required dose and release rate)

Fluid 3 (oil). An oil, immiscible with the first two fluids in which the microcapsule's "outer skin" is insoluble so that the suspended microcapsules can be delivered by injection when non-aqueous administration is required. Submersion of microcapsules in the oil also can aid the curing or polymerization of the "outer skin." A preferred example of the oil vehicle is halogenated poppy seed oil which also serves as a radiocontrast medium.

Alternate Compositions for Fluid 1

Main solvent—ethyl alcohol

Co-solvents—(co-surfactants) are normal alcohols—C4 to C8
  high dielectric constant solvents—
    tetrahydrofuran
    dioxane
    acetonitrile
    dimethylformamide
    dimethylacetamide
    dimethylsulfoxide
Oil—dense radiocontrast liquids s.a. halogenated unsaturated oils
  e.g. halogenated poppy seed oil, cotton seed oil, safflower oil, olive oil, canola oil, peanut oil, sesame oil, corn oil.
  also saturated oils can be used, s.a. heavy mineral oil, liquid petrolatum
Polymers—used to form the "outer skin" on the microcapsules
  Monoglycerides, polyglycerides,—esp. glycerol esters ranging from C12-C22,
    e.g. monostearate, distearates, monooleates, monolaurates and olive oil
  polyglycerides—cholesterol, waxy plant sterols (stigmasterol, phytosterol, campesterol)
  phospholipids—lecithins (phosphatydyl choline) and/or combinations with mono/polyglycerides
  polyvinylpyrolidone
  polyacrylates,
  PEG-hydroxypropyl methacrylate (HPMA)
  PEG 4,000-12,000
  polyethylene glycol/acrylate copolymers
  polyethylene glycol/dextran copolymers
Alternate Concentrations:

|  |  |
|---|---|
| Main solvent | 75-95% |
| Co-solvents | 1-10% |
| Oil | 1-10% |
| Polymer | 1-5% |
| Water | 1-20% |

Alternate Composition for Fluid 2
  PEG 400-20000
  Dextran (MW=40,000-100,000)
  0.9% Sodium chloride
  Sorbitan Monolaurate/20 moles Ethylene oxide
  balance is water
  Drug dissolved at saturated or specified concentration (according to required dose and release rate)
Alternate Concentrations:

|  |  |
|---|---|
| PEG | 1-5% |
| Dextran (MW = 40,000-100,000) | 5-10% |
| Sodium chloride | 0.9% |
| Sorbitan Monolaurate/20ETO | 1-5% |
| Water (balance of volume) | |
| Drug concentration saturated or specified | |

Alternate Composition for Fluid 3 (Oils)
  Dense radiocontrast liquids s.a. iodinated unsaturated oils e.g. poppy seed oil, cotton seed oil, safflower oil, olive oil, canola oil, peanut oil, sesame oil, corn oil. Also saturated oils can be used, s.a. heavy mineral oil and petrolatum.
  One hundred percent oil or a mixture may be used as a carrier vehicle for the suspended microcapsules Example IX Exemplary First Aqueous Solvent Microcapsule Formulations Alternate Method—Hydrophilic Outer Skin
  Fluid 1—(aqueous); the main solvent is a water, one or more co-solvents (which also can act as co-surfactants), and a lecithins are dissolved up to 5% w/v to form the outer skin on the microcapsules.
  An example is: 3% polyvinyl alcohol dissolved
    in a mixture of
      20% isopropyl alcohol and
      80% water
  Fluid 2 (aqueous); the main solvent is water plus surfactants (ex. polyethoxylated sorbitan esters; polyethylene glycol) and plus a polysaccharide (Dextran) and normal saline (0.9%) which helps achieve the desired critical micelle concentration.
  An example is: 1% PEG 4000
    5% Dextran-70 (MW=70,000)
    0.9% Sodium chloride
    2% Sorbitan Monooleate/20 moles Ethylene oxide
    Water (up to 100% volume)
    dissolved drug at saturated or specified concentration (according to required dose and release rate)
  Fluid 3 (aqueous)—a PEG and PVP solution which can aid the curing or polymerization of the "outer skin."
    1% Polyvinyl pyrollidone
    4% PEG 4000
    5% Dextran-70 (MW=70,000) balance is 0.9% Sodium chloride Example X Externally Triggered Microcapsules Multilayered microcapsules were formed in microgravity conditions, containing cis-platin and ferromagnetic particles obtained from Ceramic Magnetics, Inc. (Fairfield, N.J.). These ferromagnetic particles (<1μ) are composed of 66 wt % $Fe_2O_3$, 9 wt % NiO and 25 wt % ZnO. These ceramic (magnetic) particles have a Curie temperature of about 48° C. (FIG. 2). The microcapsules ranged from 10 to 100μ in diameter. Microcapsules of this size are suitable for chemoembolization of solid vascular tumors such as those in the spleen, liver, kidney or pancreas, whereby the anti-tumor drug, cis-platin in the case, can be released by exposure to an externally triggered electromagnetic field.

For use in pancreatic or liver cancer, for example, the microcapsules described in this example would be infused into a designated artery or directly injected into the tumor during a surgical procedure. The patient is subjected to an electromagnetic field of about 85-100 KHz, or a magnetic field strength of about 0.1 Tesla for a period of about 10 minutes in order to release the drug. In alternate embodiments, one could use an electromagnetic field of from about 20 to about 500 KHz.

For embodiments using a magnetic field such as described in this example, the microcapsules are designed so that the SAR of the microparticle is much greater than that of the microcapsule membrane and the tissue. Typically the SAR of the microcapsule is 2 to 4 times greater than the SAR of the outer membrane, which is 4-10 times greater than the SAR of the surrounding tissue.

Example XI

Alternative Forms of Energy for Externally Triggering Microcapsules

The microcapsules described herein may also be designed to trigger a drug release by application of radiofrequency (RF). In this case, the microcapsule is designed to have a SAR for the RF of at least 20 times greater than that of the surrounding tissues. In such applications, the microcapsules may contain internal components of high dielectric particulates, such as amorphous carbon, graphite, aluminum powder, acetylene black, a combination of TWEEN, sodium amyl alcohol, and paraffin oil, or other metallic particles dispersed throughout or surrounded by a thin layer of a lower dielectric medium that is a solid or dense gel, such as polyacrylate, nylon, or polyethyl methacrylate, for example. The use of such materials as amorphous carbon, graphite, aluminum powder, or other metallic particles as absorbers of both radiofrequency and microwave energy are described in the literature, in particular in Gautherie, 1990, pages 9-16, Chou, et al., 1984, and Guy et al., (incorporated herein in pertinent part by reference). The overall conductivity of the microparticles contained in the microspheres are at least 5 times greater than that of surrounding tissues at the wavelength used. A table of minimum conductivities follows:

TABLE 3

Minimum conductivity of microparticles inside therapeutic capsules.

| | Frequency | | | |
|---|---|---|---|---|
| | 1 MHz | 2.5 MHz | 10 MHz | 25 MHz |
| Conductivity at 37° C. (mS/meter) | 3500 | 3100 | 4000 | 4500 | mS is milliSiemens (amps/vol)

Because the microparticles are more dense than the liquid contents of the microcapsules, the microparticles sediment to the membrane. When the radiofrequency is applied, the microparticles heat much more rapidly than the membrane, thus melting a hole in the outer membrane. Often two electrodes or two planes of electrodes are used, however, individual voltage control for each set of electrodes is normally required.

In those embodiments in which microwave heating is used, the typical microwave range is from about 300 MHz to about 300 GHz. Frequencies above 2450 MHz require a shielded room to avoid interference. The same heating principles apply as described for radiofrequency, i.e. the SAR of the microparticle is much greater than the SAR of the outer membrane, which is much greater than the SAR of the surrounding tissue. Spherical microparticles may be used, however, the preferred shape of the microparticles is a tiny rod or miniature helical coil to maximize local microwave absorption and punctuate heating. The primary energy absorber in the microparticles can be made of carbon fibers, amorphous carbon, graphite particles, aluminum, acetylene black, a combination of TWEEN, sodium amyl alcohol, and paraffin oil, or other metallic particles surrounded by a ceramic, a polymer, or a dense gel that has a thermal conductivity at least 5 times greater than that of the polymer comprising the outer membrane of the microcapsule. The preferred mode is to use frequencies up to 250 GHz or greater where the quarter wavelength node is on the order of 10 microns, which is the size of the energy absorbing microparticles.

In those embodiments in which ultrasound is used to trigger the microcapsules, microspheroids containing oils or alcohols and surfactants may be made in the same manner as the primary microcapsules except that these spheroids are then coated with a layer of charged polymer that has a conductivity on the order of 5000 mS/meter or greater. Several of these microspheroids are then dispersed inside the drug carrying larger microcapsule, the outer membrane of which has a melting point at least 20° C. less than that of the outer wall of the ultrasound absorbing microspheroid. As the ultrasound is transmitted through the tissues (and the outer membrane of the microcapsules), it is absorbed by the different density phases inside the spheroids. For example, ultrasound is reflected by the more dense, conductive outer wall and thus the microspheroid heats up to a temperature above the melting temperature of the outer membrane and thus melts a hole in the microcapsule outer membrane. Typical components inside the microspheroid are amyl alcohol, sorbitan monooleate, SMO-20, oils, and other mediums that have a density significantly different from that of water (aqueous phases inside the microcapsule) and the surrounding tissues. The use of oil/graphite and other oil layers for absorption of ultrasound is described in Gautherie, 1990, pages 92-93, Madsen et al., 1982, and Lele et al., 1982, (all incorporated in pertinent part herein by reference.)

Thus the system represents an ultrasound absorbing microcapsule (microspheroid) made in the same fashion as the larger microcapsules described herein, but the microspheroids are then placed inside a therapeutic microcapsule with an outer membrane that melts at a temperature at least 20° C. below that of the microspheroid.

It is also understood that the present methods may be used in conjunction with other forms of therapy including, but not limited to hyperthermia therapy. The use of the combination of hyperthermia and chemotherapeutic drugs is discussed in Urano et al., *Local Hyperthermia in Combination with Chemotherapeutic Agents*, in *Interstitial Hyperthermia*, L. Handl-Zeller (ed.) Springer-Verlag, New York, 1992, incorporated in pertinent part herein by reference.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, one alternate embodiment includes use of aqueous-soluble cyclodextrin (in the hydrophilic phase) which has a hydrophobic center that can itself entrap hydrophobic drugs thereby acting as a carrier for hydrophobic drugs within the aqueous phase. Another alternate embodiment allows after microcapsules are formed, for ancillary polymeric outer coats to be applied by conventional methods (electrostatic coating, aerosolization and drying, etc.). This is made possible by designing the precise chemical makeup of the initial polymeric outer skin such that it will be compatible with both drug diffusion and the ancillary coating to be applied. When surfactants are used to facilitate adhesion of the third solution or ancillary coating the HLB must be selected to be compatible with the HLB of the existing outer coating which has already been formed, such that the solution containing the ancillary coating will wet the surface of the existing outer coating, to enable deposition of the ancillary coating. This is in contrast to conventional liposomes whose outer membrane composition is a variable, depending on the phase separation of the phospholipids and cholesterol adduct when each liposome forms. Another alternative embodiment incorporates an energy absorbing medium (e.g. photoactivator) which can absorb electromagnetic, ultraviolet, infrared, ultrasonic, radiofrequency and microwave radiation and thereby cause activation of a short-lived drug component just prior to administration or after the microcapsules have reached the target site. Another embodiment incorporates magnetic particles and magnetic fields or free-fluid electrophoretic mechanisms, etc. to facilitate dispersion or transport of one phase across the immiscible interface into the other phase. This has been demonstrated as a single pass, unidirectional form of mixing that is best exploited in microgravity. Another embodiment includes attachment of certain (hydrophobic) antibodies to the polymeric skin which gives the microcapsules site specificity by being able to bind to target cells (e.g. tumor) while entrapped drugs diffuse out to provide maximum doses to those cells with that antigenic site. Another embodiment makes use of polyethylene glycol (PEG) complexed to peptide or protein drugs and a customized polymeric outer skin which permits the drug-PEG complex to diffuse out of the microcapsule as an intact entity. This permits the drug to resist antibody attachment and remain in the blood stream longer as found in the Pegnology 4 type of drug complexes developed by Enzon, Inc. The improvement being delivery of this complex in the tailored microcapsules and controlled release of the complex through the specially designed polymeric outer skin. Another embodiment is microcapsules containing magnetic particles that can be heated by exposure to an electromagnetic field so that the particles are able to melt the polymer shell and release the contents without causing widespread hyperthermic damage to the surrounding tissues. Other embodiments include the use of the microcapsules of the invention for the production of crystals within an internal aqueous phase. All such modifications are intended to be included within the scope of the appended claims.

While the preferred embodiments of the invention have been shown and described, modifications thereof can be made by one skilled in the art without departing from the spirit and teachings of the inventions. The embodiments described herein are exemplary only, and are not limiting. Many variations and modifications of the invention and apparatus disclosed herein are possible and are within the scope of the inventions. Accordingly, the scope of protection is not limited by the description set out above, but is only limited by the claims which follow, that scope including all equivalents of the subject matter of the claims.

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference and to the extent that they provide materials and methods not specifically shown.

REFERENCES CITED

The following references to the extent that they provide procedural details supplementary to those set forth herein, are specifically incorporated herein by reference.

Allen, T. M. Interactions of Drug Carriers with the Mononuclear Phagocytic System, in G. Gregoriadis (Ed.) *Liposomes as Drug Carriers*, John Wiley & Sons Ltd., New York, pp. 37-50, 1988.

Allen, T. M., Mehra, T., Hansen, C. and Chin, Y. C., Stealth Liposomes: An Improved Sustained Release System for 1-b-D-Arabinofuranosylcytosine, Cancer Res. 52:2431-39, 1992.

Bhargava, H. N., Narurkar, A., and Lieb, L. M., Using Microemulsions for Drug Delivery, Pharmaceutical Technology, pp. 46-54, March 1987.

Chang, T. M. S., The in vivo effect of semi-permeable microcapsules containing L-asparaginase on 6C3HED lymphosarcoma, Nature, 229:117-178, 1971.

Chelvi, T. P. and Ralhan, R., Int. J. Hyperthermia, 11(5):685-695, 1995.

Chen, J. S. et al., Development of Ni-4 wt % Si Thermoseeds for Hyperthermia Cancer Treatment, J. Biomedical Materials Research 22:303-319, 1988.

Chou C. K. et al., Bioelectromagnetics 5:435-441, 1984.

Gabizon, A., et al., Liposome-Associated Doxorubicin: Preclinical Pharmacology and Exploratory Clinical Phase, in G. Lopez-Berestein and I. J. Fidler (Eds.) *Therapy of Infectious Diseases and Cancer*, Alan R. Liss, Inc., New York, pp. 189-203, 1992.

Gautherie M. (ed.) Methods of External Hyperthermic Heating, Springer-Verlag, New York, 1990.

Guy, A. W., IEEE Trans. Microwave Theory and Tech. 32:1182-1200.

Halbert, G. W., Stuart, J. B., Florence, A. T., The Incorporation of Lipid Soluble Antineoplastic Agents into Microemulsions-Protein-free Analogues of Low Density Lipoprotein, Int. J. Pharm. 21: 219-232, 1984.

Hand, J. W., Biophysics and Technology of Electromagnetic Hyperthermia, in Gauthereie, M., (Ed.) *Methods of External Hyperthermic Heating*, Springer-Verlag, New York, pp. 16-24, 1991.

Kakinuma, K. et al., Targeting chemotherapy for malignant brain tumors using thermosensitive liposomes and localized hyperthermia, J. Neurosurgery 84:180-184, 1996.

Kakinuma, K. et al., Drug delivery to the brain using thermosensitive liposomes and local hyperthermia, Int. J. Hyperthermia, 12:157-165, 1996.

Kimler, B. F, et al., Combination of Aziridinylbenzoquinone and Cis-platinum with Radiation Therapy in the 9L Rat Brain Tumor Model, Int. J. Radiation Oncology Biol. Phys, 26: 445-450, 1993.

Lele P. P. et al., Brit. J. Cancer 45 (Suppl V) 108:121, 1982.

Magin, R. L., Hunter, J. M., Meisman, M. R., and Bark, G. A., Effect of vesicle size on clearance, distribution and tumor uptake of temperature sensitive liposomes, Cancer Drug Delivery 3:223-237, 1986.

Madsen E. L. et al., Ultrasound Med. Biol. 8:277-287, 1982.

McCutcheon's Detergents and Emulsifiers, 1979, North American Edition, McCutcheon Division, MC Publishing Co., 175 Rock Road, Glen Rock, N.J. 07452.

Mitchell, J. B., Cook, J. A., and Russo, A., Biological Basis for Phototherapy, in Morstyn, G. and Kaye, A. H. (Eds.), Phototherapy of Cancer, Harwood Academic Pub., New York, pp. 1-22, 1990.

Morrison, D., Mosier, B., and Cassanto, J. M., Immiscible phase microencapsulation of drugs in microgravity, 6$^{th}$ International Symposium on Experimental Methods for Microgravity Materials Sciences, published by Minerals, Metals and Materials Society, Warrendale, Pa., R. A. Schiffman & J. B. Andrews, Eds., pp 199-207, 1994.

Parikl, l. and Stern, W. Microcrystal Drug Delivery System, in Harvey S. Price (Ed) *The Biotechnology Report* 1993/94, Bookbuilders, Ltd., Hong Kong, pp. 219-220, 1994.

Talsma, H. and Crommelin, D. J. A., Liposomes as Drug Delivery Systems, Part 1: Preparation. Pharmaceutical Technology, pp. 96-106, October 1992.

Wright, K. C., Wallace, S., Mosier, B. and Mosier, D., Microcapsules for Arterial Chemoembolization: Appearance and In Vitro Drug Release Characteristics, J. Microencapsulation 5:13-20, 1988.

What is claimed is:

1. A method of controlling the release of a plurality of immiscible liquids comprising the steps of:
    providing one or more microcapsules wherein the one or more microcapsules comprise:
        the plurality of immiscible liquids;
        a flexible polymer outer membrane encapsulating the liquids, the polymer outer membrane having a melting temperature; and
        one or more energy absorbing trigger particles contained in at least one of the liquids in contact with the polymer outer membrane, wherein the one or more energy absorbing trigger particles are co-encapsulated with the liquids by the flexible polymer outer membrane, wherein the one or more energy absorbing trigger particles sediment in the at least one of the liquids in contact with the polymer outer membrane, wherein at least one of the one or more energy absorbing trigger particles are in contact with the polymer outer membrane, wherein the one or more energy absorbing trigger particles have a higher specific absorption rate for radiofrequency, microwave, or ultrasound energy than the specific absorption rate of the polymer outer membrane, and wherein the temperature of the one or more energy absorbing trigger particles is increased by absorbing the energy to melt at least a portion of the polymer outer membrane;
    delivering the one or more microcapsules in tissue; and
    applying the radiofrequency, microwave, or ultrasound energy to the one or more microcapsules such that at least one of the one or more energy absorbing trigger particles in at least one of the one or more microcapsules increases in temperature by absorbing the energy thereby melting the respective polymer outer membrane of the at least one of the one or more microcapsules and thereby releasing the encapsulated immiscible liquids.

2. The method of claim 1, wherein the polymer outer membrane comprises polyvinyl alcohol and the one or more energy absorbing trigger particles comprises aluminum powder.

3. The method of claim 1, wherein the microcapsule has a diameter of from about 1 to about 500 microns.

4. The method of claim 1, wherein the microcapsule has a diameter of from about 300 to about 500 microns.

5. The method of claim 1, wherein the microcapsule has a diameter of from about 50 to about 300 microns.

6. The method of claim 1, wherein the microcapsule has a diameter of from about 30 to about 50 microns.

7. The method of claim 1, wherein the microcapsule has a diameter of from about 20 to about 30 microns.

8. The method of claim, wherein the microcapsule has a diameter of from about 1 to about 20 microns.

9. The method of claim 1, wherein the one or more microcapsules are contained in a pharmaceutically acceptable solution.

10. The method of claim 1, wherein all mixing between the immiscible liquids is substantially limited.

11. The method of claim 1, wherein the immiscible liquids comprise multi-lamellar phases.

12. The method of claim 1, wherein the one or more microcapsules is further comprised of a drug in the one or more immiscible liquids in contact with the polymer outer membrane.

13. A method of controlling the release of one or more immiscible liquid phases comprising the steps of:
    providing one or more microcapsules comprised of:
        the one or more immiscible liquid phases, wherein the liquid phases are comprised of at least one aqueous phase and at least one hydrocarbon phase;
        a flexible polymer outer membrane encapsulating the one or more liquid phases, the polymer outer membrane having a melting temperature; and
        one or more energy absorbing trigger particles in at least one of the one or more liquid phases in contact with the polymer outer membrane, wherein the one or more energy absorbing trigger particles sediment in the at least one of the one or more liquid phases in contact with the polymer outer membrane, and wherein at least one of the one or more energy absorbing trigger particles is in contact with the polymer outer membrane, wherein the one or more energy absorbing trigger particles have a higher specific absorption rate for radiofrequency, microwave, or ultrasound energy than the specific absorption rate of the polymer membrane, and wherein the temperature of the one or more energy absorbing components is increased by absorbing the energy to melt at least a portion of the polymer outer membrane;
    delivering the one or more microcapsules in tissue; and
    applying the radiofrequency, microwave, or ultrasound energy to the one or more microcapsules such that at least one of the one or more energy absorbing trigger particles in at least one of the one or more microcapsules increases in temperature by absorbing the energy thereby melting the respective polymer outer membrane of the at least one of the one or more microcapsules and thereby releasing the encapsulated immiscible liquids.

14. A method of controlling the release of one or more immiscible liquids comprising the steps of:
    providing one or more microcapsules wherein the one or more microcapsules comprise:
        one or more immiscible liquids;
        a flexible polymer outer membrane encapsulating the liquids, the polymer outer membrane having a melting temperature; and
        one or more energy absorbing trigger particles containing a radiocontrast media, wherein the one or more energy absorbing trigger particles are contained in at least one of the one or more liquids in contact with the polymer outer membrane, wherein the one or more energy absorbing trigger particles sediment in the at least one of the one or more liquids in contact with the polymer outer membrane, and wherein at least one of the one or more energy absorbing trigger particles is in contact with the polymer outer membrane, wherein the one or more energy absorbing trigger particles have a higher specific absorption rate for radiofrequency, microwave, or ultrasound energy than the specific absorption rate of the polymer outer membrane, and wherein the temperature of the one or more energy absorbing trigger particles is increased by absorbing the energy to melt at least a portion of the polymer outer membrane;
    delivering the one or more microcapsules in tissue; and applying the radiofrequency, microwave, or ultrasound energy to the one or more microcapsules such that at least one of the one or more energy absorbing trigger particles in at least one of the one or more microcapsules increases in temperature by absorbing the energy thereby melting the respective polymer outer membrane of the at least one of the one or more microcapsules and thereby releasing the encapsulated one or more immiscible liquids.

15. The method of claim 14, wherein the radiocontrast media is a halogenated oil, wherein the one or more energy absorbing trigger particles comprises aluminum powder, and wherein the flexible polymer outer membrane comprises polymer alcohol.

16. The method of claim 15 wherein the halogenated oil is poppy seed oil, cotton seed oil, soybean oil, safflower oil, corn oil, sunflower seed oil, sesame seed oil, or canola oil.

17. The method of claim 15, wherein the halogenated oil is iodinated poppy seed oil.

18. A method of controlling the release of two to four immiscible liquid phases comprising the steps of:
providing one or more microcapsules wherein the one or more microcapsules comprise:
the two to four immiscible liquid phases;
a flexible polymer outer membrane encapsulating the liquid phases, the polymer outer membrane having a melting temperature;
an energy absorbing trigger particle in a liquid phase in contact with the polymer outer membrane; and
a drug, in a liquid phase not in contact with the polymer outer membrane;
delivering the one or more microcapsules in tissue; and
applying radiofrequency, microwave, or ultrasound energy to the one or more microcapsules such that at least one of the one or more energy absorbing trigger particles in at least one of the one or more microcapsules increases in temperature by absorbing the energy thereby melting the respective polymer outer membrane of the at least one of the one or more microcapsules and thereby releasing the encapsulated one or more immiscible liquids;
wherein the energy absorbing trigger particle sediments in the liquid phase in contact with the polymer outer membrane,
wherein the energy absorbing trigger particle is in contact with the polymer outer membrane, and
wherein the energy absorbing trigger particle has a higher specific absorption rate for the radiofrequency, microwave, or ultrasound energy than the specific absorption rate of the polymer outer membrane.

19. The method of claim 18, wherein the flexible polymer membrane comprises polymer alcohol and the one or more energy absorbing trigger particles comprises aluminum powder.

* * * * *